United States Patent
Schlam et al.

(10) Patent No.: US 12,129,264 B2
(45) Date of Patent: Oct. 29, 2024

(54) CRYSTALLINE FORMS OF A PAR4 INHIBITOR

(71) Applicant: BRISTOL-MYERS SQUIBB COMPANY, Princeton, NJ (US)

(72) Inventors: Roxana F. Schlam, Hod Hasharon (IL); Nicolas Cuniere, Belle Mead, NJ (US); Victoria A. Mbachu, Somerset, NJ (US); Zhongping Shi, Plainsboro, NJ (US); Petinka I. Vlahova, West Lafayette, IN (US)

(73) Assignee: Bristol-Myers Squibb Company, Princeton, NJ (US)

( * ) Notice: Subject to any disclaimer, the term of this patent is extended or adjusted under 35 U.S.C. 154(b) by 801 days.

(21) Appl. No.: 17/415,237

(22) PCT Filed: Dec. 20, 2019

(86) PCT No.: PCT/US2019/067717
§ 371 (c)(1),
(2) Date: Jun. 17, 2021

(87) PCT Pub. No.: WO2020/132381
PCT Pub. Date: Jun. 25, 2020

(65) Prior Publication Data
US 2022/0064186 A1 Mar. 3, 2022

Related U.S. Application Data

(60) Provisional application No. 62/783,223, filed on Dec. 21, 2018.

(51) Int. Cl.
*C07D 513/04* (2006.01)
*A61K 31/433* (2006.01)
*A61K 45/06* (2006.01)
*A61P 7/02* (2006.01)
*C07C 55/10* (2006.01)
*C07C 59/265* (2006.01)

(52) U.S. Cl.
CPC .......... *C07D 513/04* (2013.01); *A61K 31/433* (2013.01); *A61K 45/06* (2013.01); *A61P 7/02* (2018.01); *C07C 55/10* (2013.01); *C07C 59/265* (2013.01); *C07B 2200/13* (2013.01)

(58) Field of Classification Search
CPC .......................... C07D 513/04; A61K 31/433
See application file for complete search history.

(56) References Cited

U.S. PATENT DOCUMENTS

| | | |
|---|---|---|
| 9,688,695 B2 | 6/2017 | Banville et al. |
| 10,047,103 B2 | 8/2018 | Banville et al. |
| 10,428,077 B2 | 10/2019 | Banville et al. |
| 10,822,343 B2 | 11/2020 | Banville et al. |

FOREIGN PATENT DOCUMENTS

WO 2013163279 A1 10/2013

OTHER PUBLICATIONS

China Doctoral Dissertations Full Text Database, Engineering Science and Technology I, No. 8 (2022).
Takata, N., Cocrystal, Pharm Tech Japan, vol. 25 (12), pp. 155-166 (2009).
Tilborg A. et al, European Journal of Medicinal Chemistry, vol. 74, pp. 411-426 (2014).
Bioavailability BMS 986141, A Randomized Study to Evaluate the Bioavailability of BMS-986141 from a Citric-acid Co-crystal Tablet Formulation Relative to the SDD Reference Tablet in Healthy Participants, (2019).
BMS-986141 Accession No. DB14942, CAS No. 1478711-48-6, (2019).
Coughlin et al., "Thrombin signaling and protease-activated receptors", Nature, 407:258-264 (2000).
Tricoci et al. "Thrombin-Receptor Antagonist Vorapaxar in Acute Coronary Syndromes", N. Eng. J. Med., 366(1):20-33 (2012).
Yadav et al., "Co-Crystals: A Novel Approach to Modify Physicochemical Properties of Active Pharmaceutical Ingredients", Indian Journal of Pharmaceutical Science, vol. 71(4), pp. 359-370 (2011).
Brittain, H. G., "Polymorphism in Pharmceutical Solids", Drugs and Pharmaceutical Sciences, vol. 192, pp. 1-210, 2009.

*Primary Examiner* — Bruck Kifle
(74) *Attorney, Agent, or Firm* — Mary K. VanAtten

(57) ABSTRACT

The present invention relates to co-crystals of the compound of formula (I), wherein the co-former molecule is succinic acid or citric acid, processes for the preparation of the co-crystal, pharmaceutical compositions thereof, and methods of using the co-crystals for treating or preventing thromboembolic disorders.

16 Claims, 16 Drawing Sheets

CRYSTALLINE FORMS OF A PAR4 INHIBITOR

CROSS REFERENCE TO RELATED APPLICATIONS

This application is a 371 application of PCT/US2019/067717, filed Dec. 20, 2019, which is entitled to priority pursuant to 35 U.S.C. § 119(e) to U.S. provisional patent application No. 62/783,223, filed Dec. 21, 2018, which is incorporated herein in its entirety.

FIELD OF THE INVENTION

The present invention relates to co-crystals of the protease activated receptor-4 (PAR4) antagonist, 4-(4-(((6-Methoxy-2-(2-methoxyimidazo[2,1-b][1,3,4]thiadiazol-6-yl)benzofuran-4-yl)oxy)methyl)thiazol-2-yl)-N,N-dimethylbenzamide. The present invention also relates to processes of making, pharmaceutical compositions, and methods of using the co-crystals of the present invention.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S.R., Nature, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., N. Eng. J. Med., 366(1):20-33 (2012). Thus, there remains a need to discover new antiplatelet agents with increased efficacy and reduced bleeding side effects.

The compound of formula (I), 4-(4-(((6-Methoxy-2-(2-methoxyimidazo[2,1-b][1,3,4]thiadiazol-6-yl)benzofuran-4-yl)oxy)methyl)thiazol-2-yl)-N,N-dimethylbenzamide (Compound (I)), is a PAR4 inhibitor, and its synthesis, and preparation as a free form solid material, and use are described in WO2013/163279.

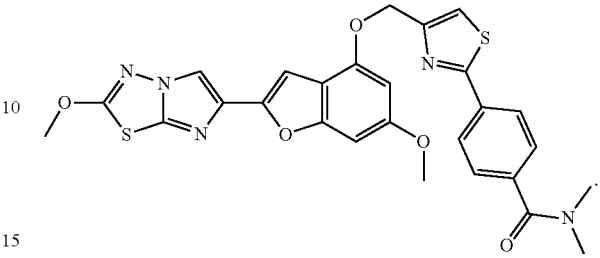

(I)

SUMMARY OF THE INVENTION

The invention is directed to co-crystals comprising the compound of formula (I),

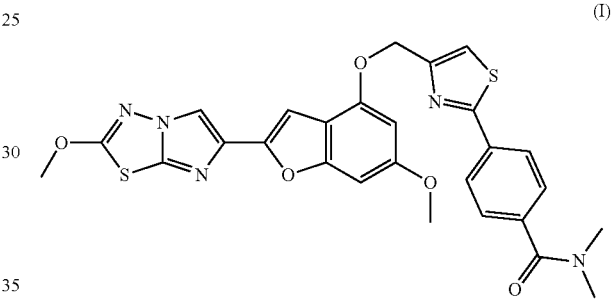

(I)

and succinic or citric acid, pharmaceutical compositions comprising the same, and treatment or prophylaxis of a thromboembolic disorder by administering an effective amount of the co-crystal to a patient or mammal in need thereof.

DETAILED DESCRIPTION

In one embodiment of the present invention is a co-crystal of the compound of formula (I) and a co-former, wherein the co-former is a citric acid or a succinic acid

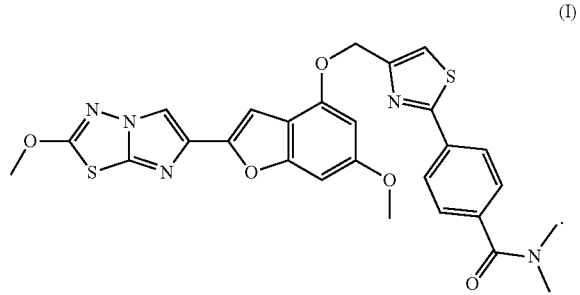

(I)

In another embodiment of the present invention, the co-former is succinic acid.

In another embodiment, the co-crystal of the compound of formula (I) and succinic acid is characterized by one or more of the following:
a) single crystal structure having unit cell parameters substantially equal to

Figure 1:
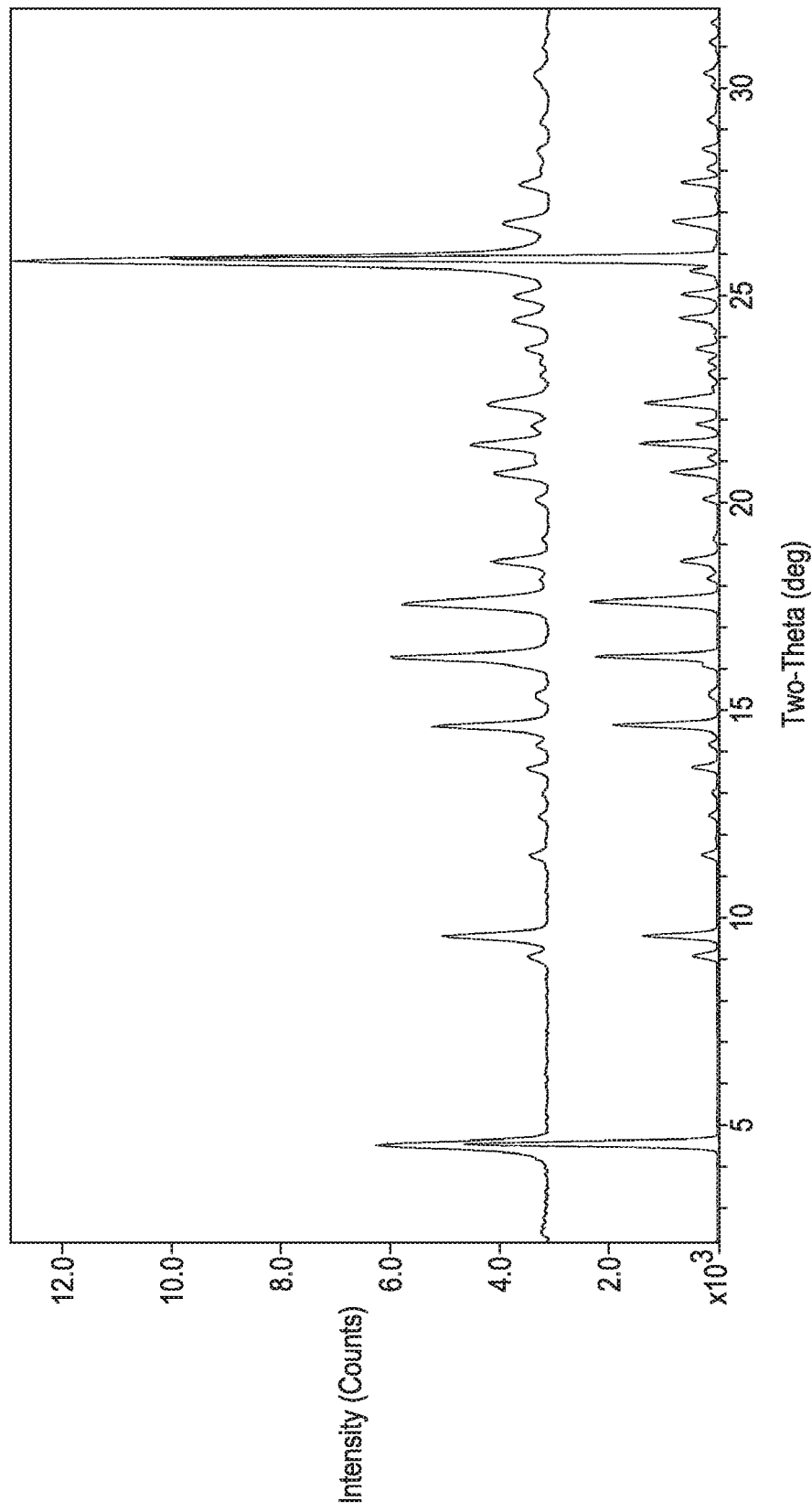
FIG. 1 shows the simulated (bottom, calculated from atomic coordinates generated at room temperature) and experimental (top) PXRD patterns for the succinic acid co-crystal of the compound of formula (I).
Figure 5:
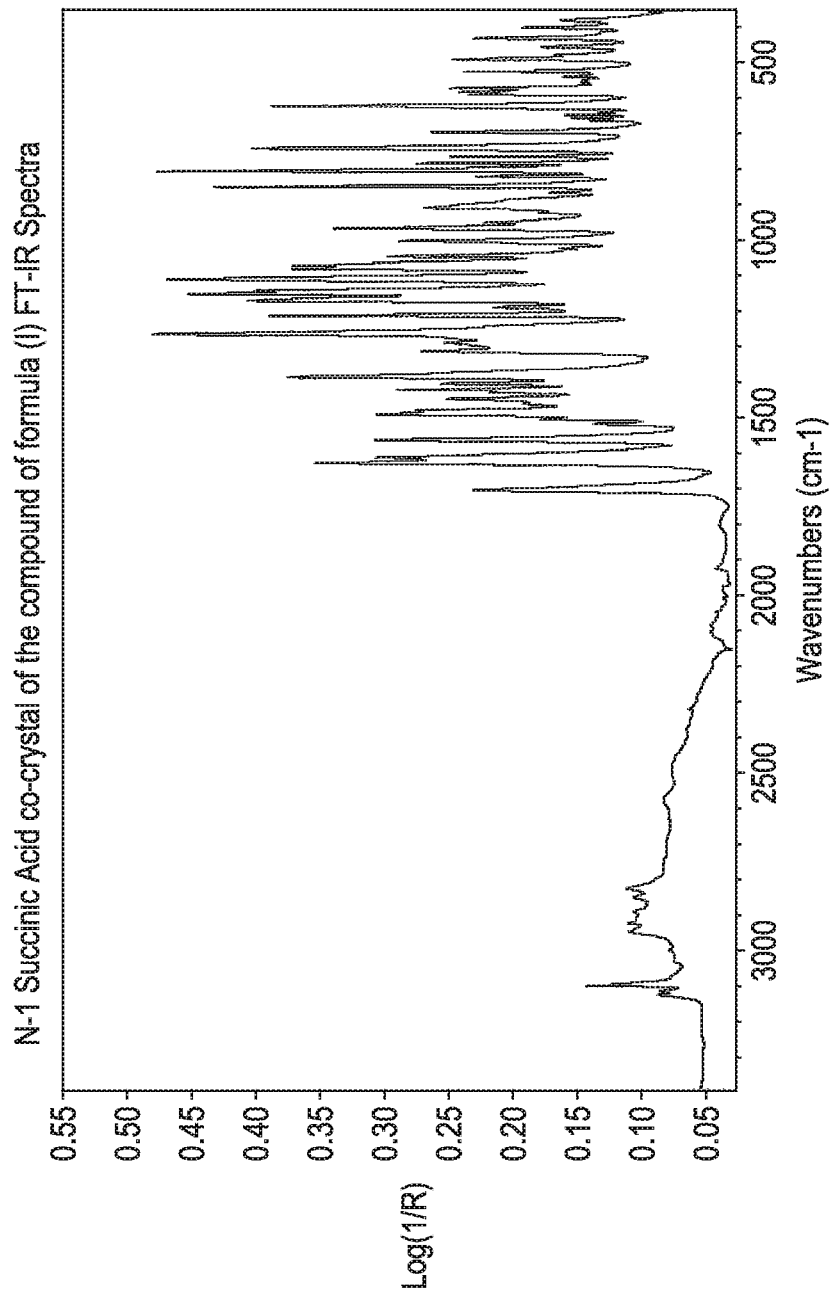
FIG. 5 shows the FT-IR spectrum of the succinic acid co-crystal of the compound of formula (I).
Figure 6:
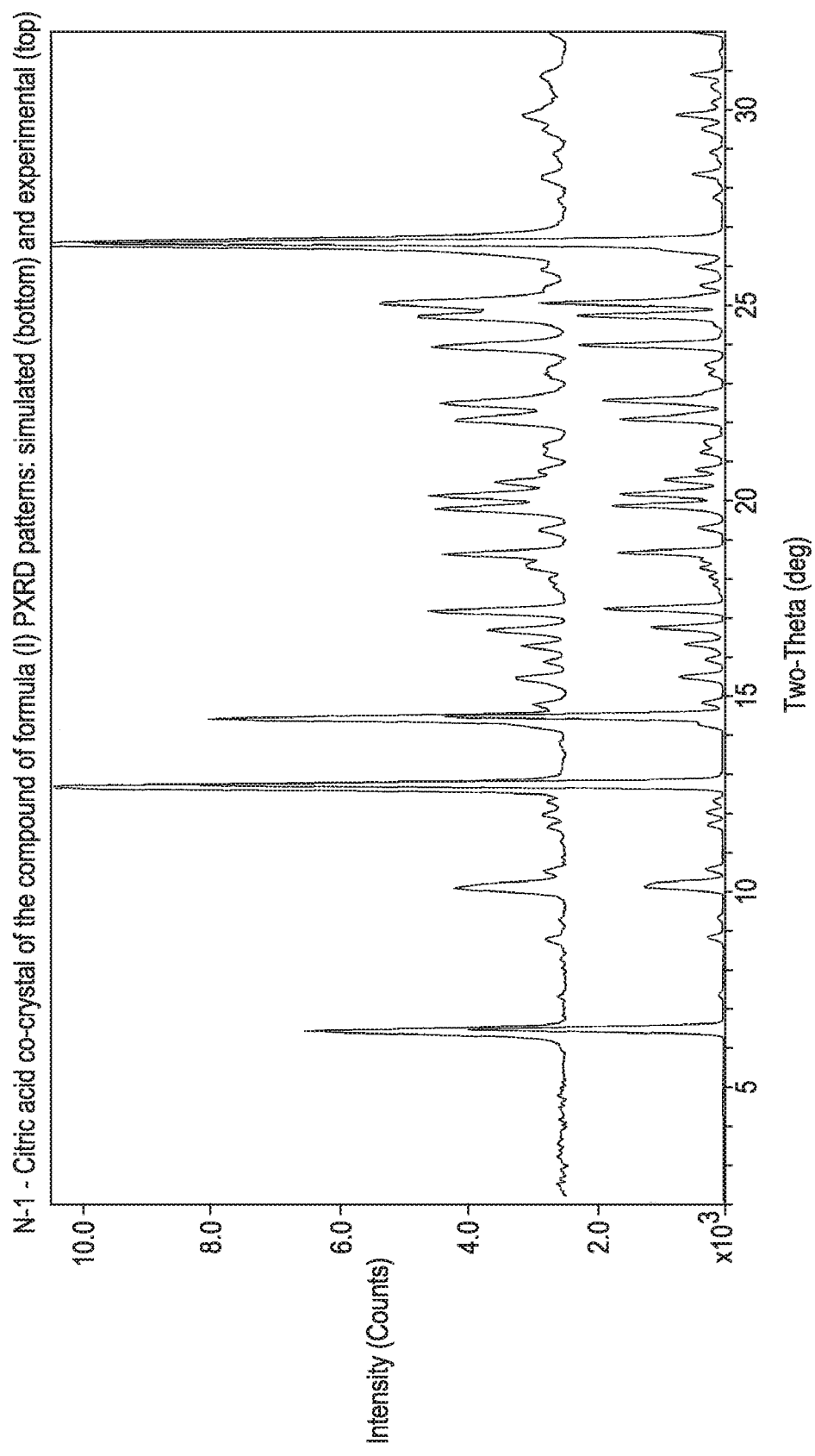
FIG. 6 shows the simulated (bottom, calculated from atomic coordinates generated at room temperature) and experimental (top) PXRD patterns for the N-1 form of the citric acid co-crystal of the compound of formula (I).

| Crystal system, space group | Triclinic, P-1 | |
|---|---|---|
| Unit cell dimensions | a = 7.5 ± 0.5Å | alpha = 103 ± 1° |
| | b = 9.6 ± 0.5 Å | beta = 92 ± 1° |
| | c = 20.1 ± 0.5 Å | gamma = 98 ± 1° |
| Volume | 1401 ± 30 Å$^3$ | |
| formula units per unit cell | 2 | |
| Temperature | room temperature | | wherein measurement of the single crystal structure is at room temperature;
b) an observed PXRD pattern substantially as shown in FIG. 1;
c) a PXRD pattern comprising 4 or more 2θ values selected from 4.5±0.2, 9.5±0.2, 14.6±0.2, 16.3±0.2, 17.6±0.2, 21.4±0.2, 22.4±0.2, and 25.9±0.2 (obtained at room temperature and (CuKα 2=1.5418 Å);
d) an infrared spectra substantially as shown in FIG. 5; and/or
e) a FT-Raman spectra substantially as shown in FIG. 6.

In another embodiment, the co-crystal of the compound of formula (I) and succinic acid has a ratio of the compound of formula (I) to succinic acid of 1: 0.5.

In another embodiment of the present invention, the co-former is citric acid.

In another embodiment, the co-crystal of the compound of formula (I) and citric acid is in the N-1 form and is characterized by one or more of the following:
a) single crystal structure having unit cell parameters substantially equal to

| Crystal system, space group | Triclinic, P-1 | |
|---|---|---|
| Unit cell dimensions | a = 10.3 ± 0.5 Å | alpha = 94 ± 1° |
| | b = 12.3 ± 0.5 Å | beta = 98 ± 1° |
| | c = 13.9 ± 0.5 Å | gamma = 98 ± 1° |
| Volume | 1717 ± 30 Å$^3$ | |
| formula units per unit cell | 2; | |
| Temperature | room temperature; | | b) a PXRD pattern substantially as shown in FIG. 6; and/or
c) a powder x-ray diffraction pattern comprising four or more 2θ values (CuKα 2=1.5418 Å at room temperature) selected from 6.4±0.2, 12.7±0.2. 14.4±0.2, 17.1±0.2, 23.9±0.2, 25.0±0.2, and 26.6±0.2.

In another embodiment of the invention, the co-crystal of the compound of formula (I) and citric acid has a ratio of 1:1.

In another embodiment of the invention, the co-crystal of the compound of formula (I) and citric acid consists essentially of Form N-1.

In another embodiment of the invention, the co-crystal of the compound of formula (I) and citric acid comprises Form N-1.

In another embodiment, the co-crystal of the compound of formula (I) and citric acid is in the N-2 form and is characterized by one or more of the following:
a) single crystal structure having unit cell parameters substantially equal to

Figure 12:
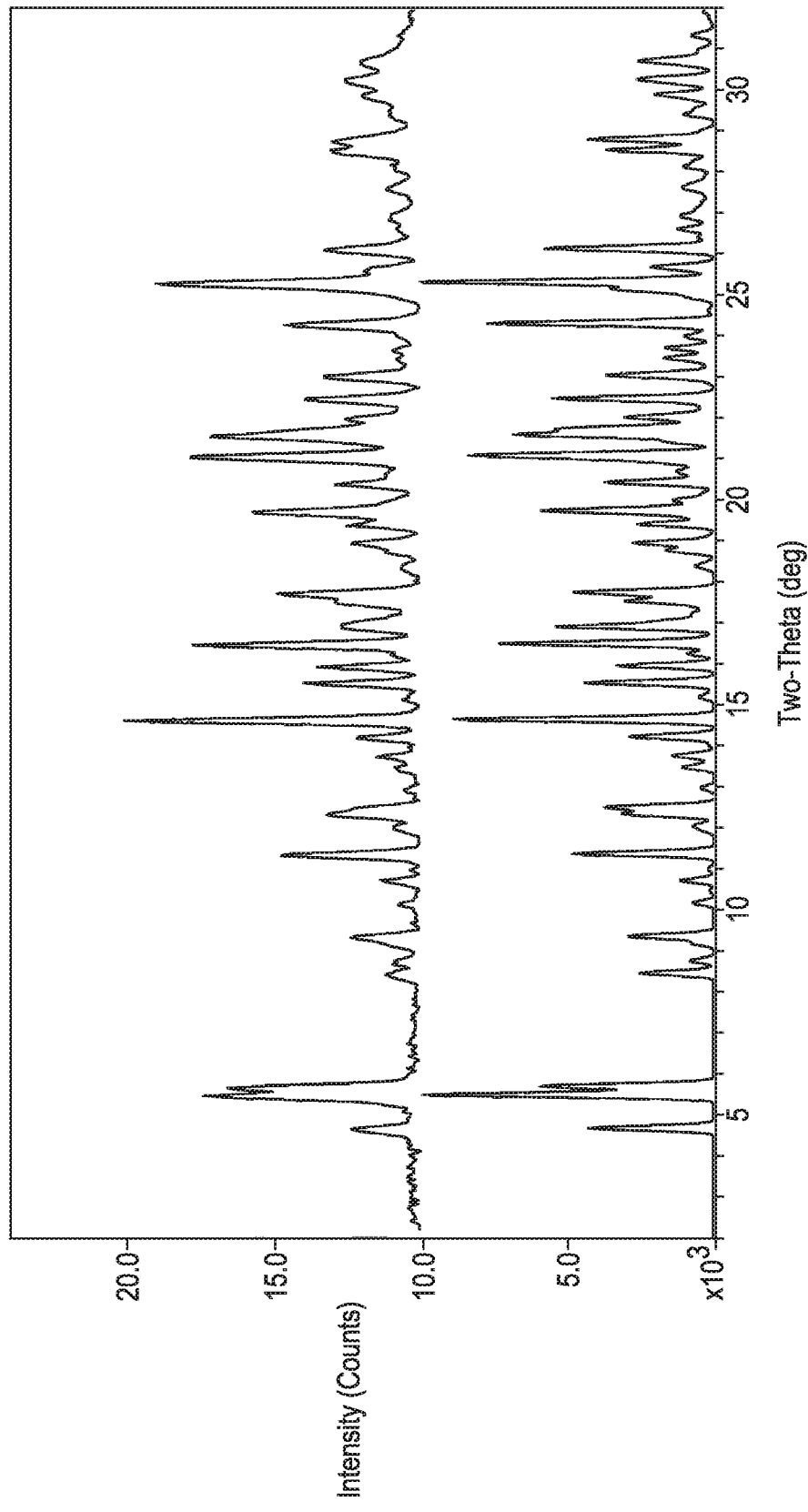
FIG. 12 shows the simulated (bottom, calculated from atomic coordinates generated at room temperature) and experimental (top) PXRD patterns of the N-2 form of the citric acid co-crystal of the compound of formula (I).

| Crystal system, space group | Triclinic, P-1 | |
|---|---|---|
| Unit cell dimensions | a = 10.4 ± 0.5 Å | alpha = 111 ± 1° |
| | b = 17.8 ± 0.5 Å | beta = 93 ± 1° |
| | c = 20.5 ± 0.5 Å | gamma = 102 ± 1° |
| Volume | 3462 ± 30 Å$^3$; | |
| Temperature | room temperature; | |
| formula units per unit cell | 4; | | b) a PXRD pattern substantially as shown in FIG. 12; and/or
c) a powder x-ray diffraction pattern comprising four or more 2θ values (CuKα λ=1.5418 Å at room temperature) selected from 4.6±0.2, 5.5±0.2, 8.4±0.2, 11.3±0.2, 14.6±0.2, 16.4±0.2, 21.0±0.2, 24.2±0.2, and 25.2±0.2.

In another embodiment of the invention, the N-1 form of the co-crystal of the compound of formula (I) and citric acid has a ratio of 1:1.

In another embodiment of the invention, the N-2 form of the co-crystal of the compound of formula (I) and citric acid has a ratio of 1:1.

In another embodiment of the invention, the co-crystal of the compound of formula (I) and citric acid consists essentially of Form N-2.

In another embodiment of the invention, the co-crystal of the compound of formula (I) and citric acid comprises Form N-2.

In another embodiment of the invention, the present invention is directed to any one of the co-crystals in substantially pure form.

In another embodiment of the invention, the succinic acid co-crystal is characterized by a PXRD having 4 or more, 5 or more, or 6 or more, 2θ values selected from 4.5±0.2, 9.5±0.2, 14.6±0.2, 16.3±0.2, 17.6±0.2, 21.4±0.2, 22.4±0.2, and 25.9±0.2 (CuKα λ=1.5418 Å at room temperature).

In another embodiment of the invention, the succinic acid co-crystal is characterized by a PXRD having at least one or more 2θ values selected from 4.5±0.2, 9.5±0.2, 14.6±0.2, 16.3±0.2, 17.6±0.2, 21.4±0.2, 22.4±0.2, and 25.9±0.2 (CuKα 2=1.5418 Å at room temperature).

In another embodiment of the invention, the succinic acid co-crystal is characterized by a PXRD having 4 or more, or 5 or more, 2θ values selected from 4.5±0.2, 9.5±0.2, 14.6±0.2, 16.3±0.2, 17.6±0.2, and 25.9±0.2 (CuKα λ=1.5418 Å at room temperature).

In another embodiment of the invention, the succinic acid co-crystal is characterized by a PXRD having 4 or more, or 5 or more, or 6 or more, 2θ values selected from 4.5±0.2, 9.5±0.2, 14.6±0.2, 16.3±0.2, 17.6±0.2, and 25.9±0.2 (CuKα λ=1.5418 Å at room temperature).

In another embodiment of the invention, the succinic acid co-crystal has single crystal structure having unit cell parameters substantially equal to

| | |
|---|---|
| Temperature | room temperature |
| Crystal system, space group | Triclinic, P-1 |
| Unit cell dimensions | a = 7.5 ± 0.5Å   alpha = 103 ± 1° |
| | b = 9.6 ± 0.5 Å   beta = 92 ± 1° |
| | c = 20.1 ± 0.5 Å   gamma = 98 ± 1° |
| Volume | 1401 ± 30 Å³ |
| formula units per unit cell | 2. |

In another embodiment, the succinic acid co-crystal is characterized by a FT-IR substantially in accordance with FIG. 5. In another embodiment, the succinic acid co-crystal is characterized by a FT-IR spectrum having peaks at 1627.9, 1704.4, and 3102.1 cm⁻¹ (+0.4 cm⁻¹).

Figure 4:
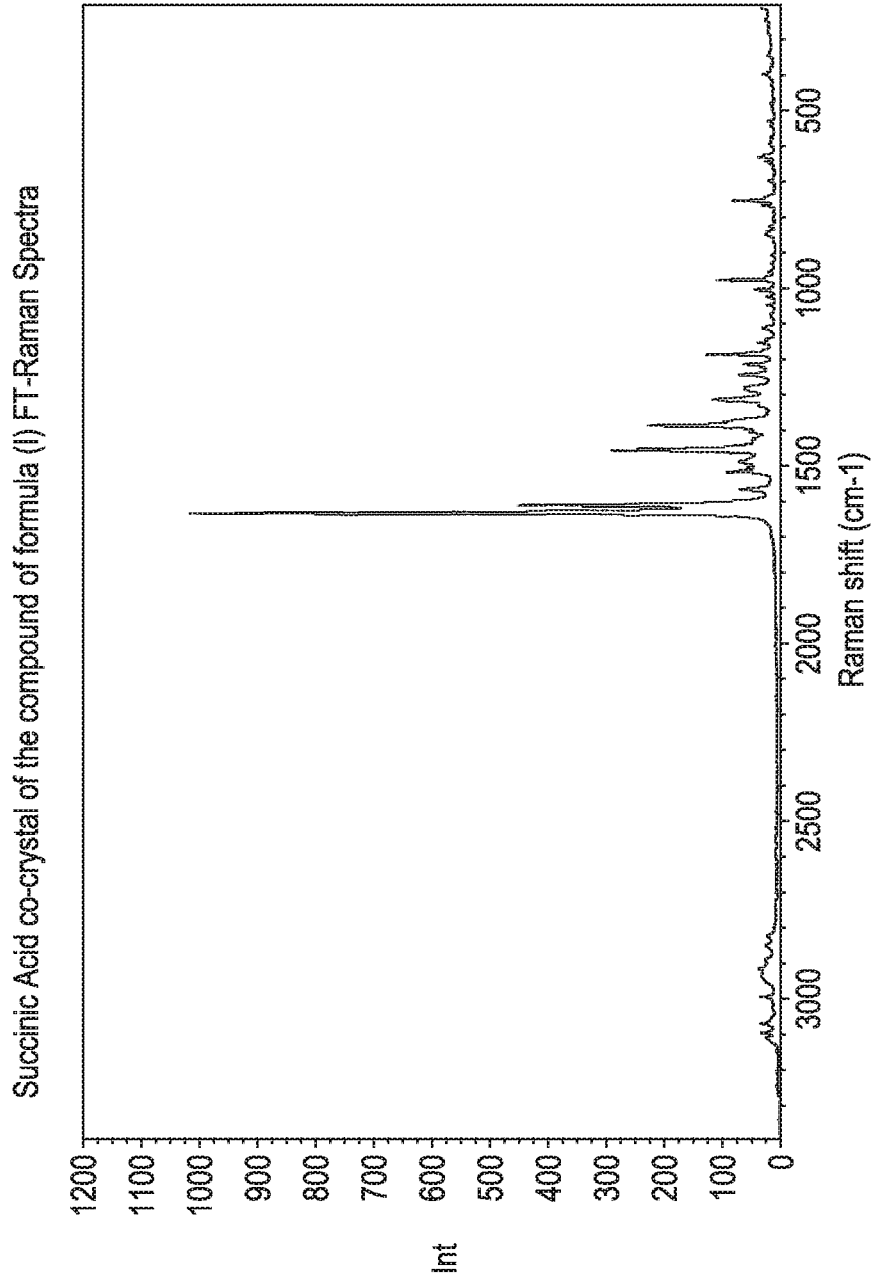
FIG. 4 shows the FT-Raman spectrum of the succinic acid co-crystal of the compound of formula (I).

In another embodiment, the succinic acid co-crystal is characterized by a FT-Raman substantially in accordance with FIG. 4. In another embodiment, the succinic acid co-crystal is characterized by a FT—Raman spectrum having peaks at 975.3, 1185.0, 1242.9, 1455.6, and 3104.4 cm⁻¹ (+0.3 cm⁻¹).

In another embodiment, the N-1 form of the citric acid co-crystal is characterized by a PXRD substantially in accordance with FIG. 6. In another embodiment, the N-1 form of the citric acid co-crystal is characterized by a PXRD having 4 or more, or 5 or more, or 6 or more, 2θ values selected from 6.4±0.2, 12.7±0.2. 14.4±0.2, 17.1±0.2, 23.9±0.2, 25.0±0.2, and 26.6±0.2 (CuKα 2=1.5418 Å at room temperature). In another embodiment, the N-1 form of the citric acid co-crystal is characterized by a PXRD having at least one or more 2θ values selected from 6.4±0.2, 12.7±0.2. 14.4±0.2, 17.1±0.2, 23.9±0.2, 25.0±0.2, and 26.6±0.2 (CuKα 2=1.5418 Å at room temperature). In another embodiment, the N-1 form of the citric acid co-crystal is characterized by a PXRD comprising 2θ values selected from 6.4±0.2, 12.7±0.2. 14.4±0.2, and 26.6±0.2 (CuKα 2=1.5418 Å at room temperature).

In another embodiment, the N-1 form of the citric acid co-crystal has single crystal structure having unit cell parameters substantially equal to single crystal structure having unit cell parameters substantially equal to

| | |
|---|---|
| Temperature | room temperature |
| Crystal system, space group | Triclinic, P-1 |
| Unit cell dimensions | a = 10.3 ± 0.5 Å   alpha = 94 ± 1° |
| | b = 12.3 ± 0.5 Å   beta = 98 ± 1° |
| | c = 13.9 ± 0.5 Å   gamma = 98 ± 1° |
| Volume | 1717 ± 30 Å³ |
| formula units per unit cell | 2. |

Figure 11:
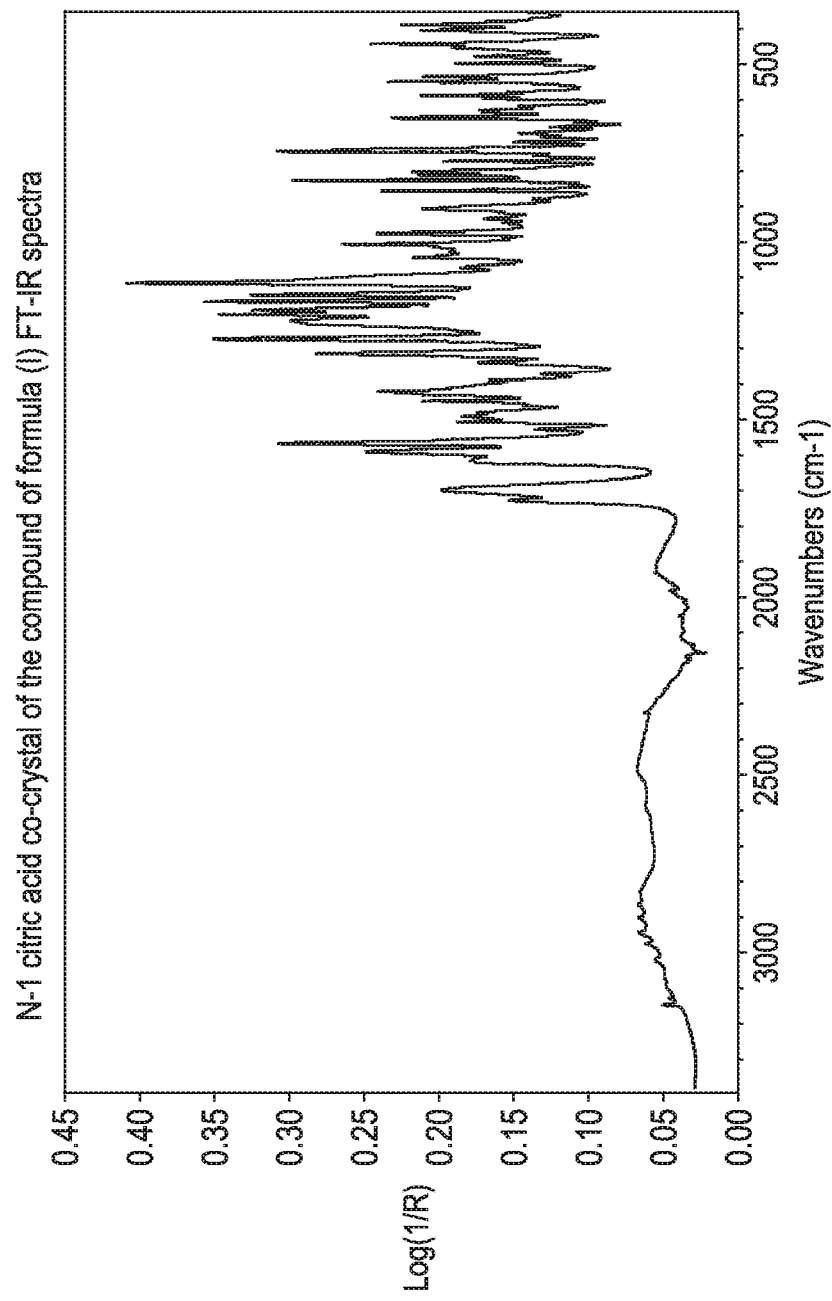
FIG. 11 shows the FT-IR of the N-1 form of the citric acid co-crystal of the compound of formula (I).

In another embodiment, the N-1 form of the citric acid co-crystal is characterized by a FT-IR substantially in accordance with FIG. 11. In another embodiment, the N-1 form of the citric acid co-crystal is characterized by a FT-IR spectrum having peaks at peaks at 1585.7, 1725.9, and 3150.5 cm⁻¹ (+0.4 cm⁻¹).

Figure 9:
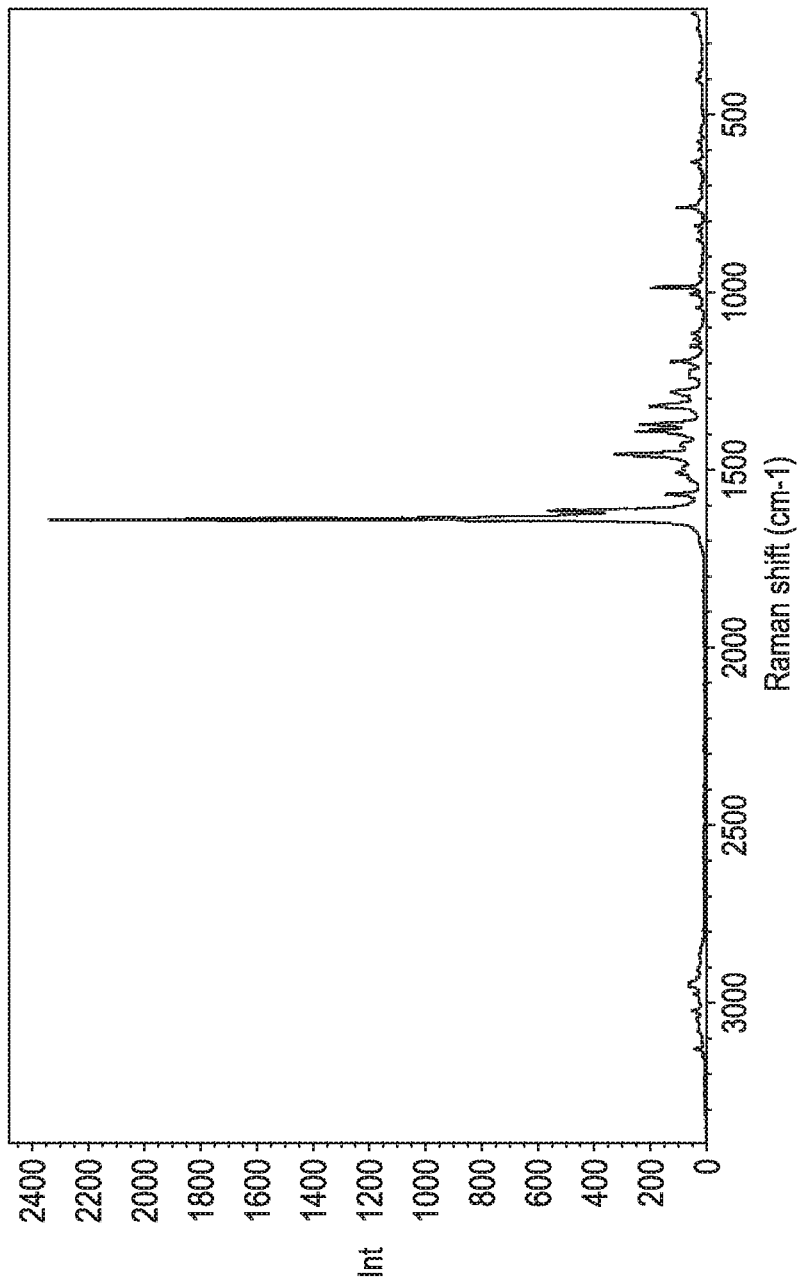
FIG. 9 shows the FT-Raman of the N-1 form of the citric acid co-crystal of the compound of formula (I).
Figure 10:
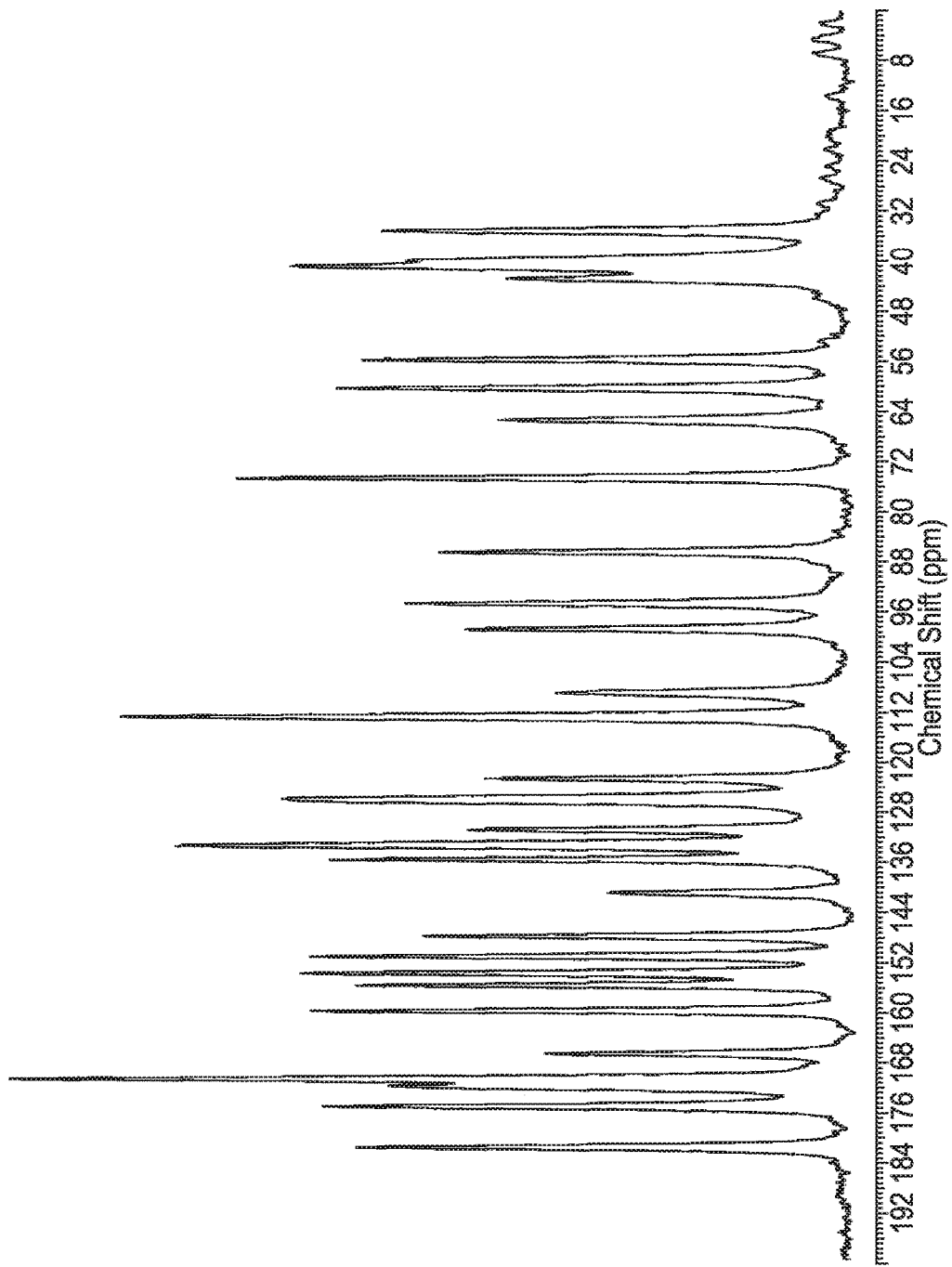
FIG. 10 shows the C-13 CPMAS SSNMR of the N-1 form of the citric acid co-crystal of the compound of formula (I).

In another embodiment, the N-1 form of the citric acid co-crystal is characterized by a FT-Raman substantially in accordance with FIG. 9. In another embodiment, the N-1 form of the citric acid co-crystal is characterized by a FT-Raman spectrum having peaks at 755.3, 807.7, 982.1, 1191.2, 1367.8, 1450.6, and 2978.9 cm⁻¹ (+0.3 cm⁻¹).

In another embodiment, the N-2 form of the citric acid co-crystal is characterized by a PXRD substantially in accordance with FIG. 12. In another embodiment, the N-2 form of the citric acid co-crystal is characterized by a PXRD having 4 or more, or 5 or more, or 6 or more, 2θ values selected from 4.6±0.2, 5.5±0.2, 8.4±0.2, 11.3±0.2, 14.6±0.2, 16.4±0.2, 21.0±0.2, 24.2±0.2, and 25.2±0.2 In another embodiment, the N-2 form of the citric acid co-crystal is characterized by a PXRD having at least one or more 2θ values selected from 4.6±0.2, 5.5±0.2, 8.4±0.2, 11.3±0.2, 14.6±0.2, 16.4±0.2, 21.0±0.2, 24.2±0.2, and 25.2±0.2 In another embodiment, the N-1 form of the citric acid co-crystal is characterized by a PXRD comprising 2θ values selected from 4 or more, or 5 or more, 2θ values selected from 4.6±0.2, 14.6±0.2, 16.4±0.2, 21.010.2, and 25.2±0.2. (Cukα λ=1.5418 Å at room temperature).

In another embodiment, the N-2 form of the citric acid co-crystal has single crystal structure having unit cell parameters substantially equal to

| | |
|---|---|
| Temperature | room temperature |
| Crystal system, space group | Triclinic, P-1 |
| Unit cell dimensions | a = 10.4 ± 0.5 Å   alpha = 111± 1° |
| | b = 17.8 ± 0.5 Å   beta = 93 ± 1° |
| | c = 20.5 ± 0.5 Å   gamma = 102 ± 1° |
| Volume | 3462 ± 30 Å³ |
| formula units per unit cell | 4. |

In another embodiment, the present invention describes a pharmaceutical composition comprising a therapeutically effective amount of at least one of the co-crystal forms of the compound of Formula (I) and a pharmaceutically acceptable carrier.

In another embodiment, the present invention describes a method for the treatment of a thromboembolic disorder which comprises administering to a host in need of such treatment a therapeutically effective amount of at least one of the co-crystal forms of the compound of Formula (1).

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are FXa inhibitors or thrombin inhibitors. Preferably, the FXa inhibitors are apixaban or rivaroxaban. Preferably, the thrombin inhibitor is dabigatran.

In some embodiments, the present invention provides a method for the treatment or prophylaxis of a thromboembolic disorder which includes the step of administering to a subject (for example, a human) in need of such treatment or prophylaxis a therapeutically effective amount of at least one of the co-crystal forms of the compound of Formula (I) disclosed herein, for example, the succinic acid co-crystal, the citric acid co-crystal, the citric acid co-crystal N-1, or the citric acid co-crystal N-2.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one of the co-crystal forms of the compound of formula (I) disclosed herein, for example, the succinic acid co-crystal, the citric acid co-crystal, the citric acid co-crystal N-1, or the citric acid co-crystal N-2, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one of the co-crystal forms of the compound of Formula (I) disclosed herein, for example, the succinic acid co-crystal, the citric acid co-crystal, the citric acid co-crystal N-1, or the citric acid co-crystal N-2, wherein the thromboembolic disorder is selected from the group consisting of acute coronary syndrome, unstable angina, stable angina, ST-elevated myocardial infarction, non-ST-elevated myocardial infarction, atrial fibrillation, myocardial infarction, transient ischemic attack, stroke, atherosclerosis, peripheral arterial disease, venous thrombosis, deep vein thrombosis, thrombophlebitis, arterial embolism, coronary arterial thrombosis, cerebral arterial thrombosis, cerebral embolism, kidney embolism, pulmonary embolism, cancer-related thrombosis, and thrombosis resulting from medical implants, devices, and procedures in which blood is exposed to an artificial surface that promotes thrombosis.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one of the co-crystal forms of the compound of Formula (I) disclosed herein, for example, the succinic acid co-crystal, the citric acid co-crystal, the citric acid co-crystal N-1, or the citric acid co-crystal N-2, wherein the thromboembolic disorder is selected from the group consisting of acute coronary syndrome, unstable angina, stable angina, ST-elevated myocardial infarction, and non-ST-elevated myocardial infarction.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one of the co-crystal forms of the compound of Formula (I) disclosed herein, for example, the succinic acid co-crystal, the citric acid co-crystal, the citric acid co-crystal N-1, or the citric acid co-crystal N-2, wherein the thromboembolic disorder is selected from the group consisting of transient ischemic attack and stroke.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one of the co-crystal forms of the compound of Formula (I) disclosed herein, for example, the succinic acid co-crystal, the citric acid co-crystal, the citric acid co-crystal N-1, or the citric acid co-crystal N-2, or solvates thereof, wherein the thromboembolic disorder is peripheral arterial disease.

In some embodiments, the present invention includes a method as described above: wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of one of the co-crystal forms of the compound of Formula (I) disclosed herein, for example, the succinic acid co-crystal, the citric acid co-crystal, the citric acid co-crystal N-1, or the citric acid co-crystal N-2.

In still yet an even further embodiment, the individual co-crystal forms of Compound (I) are substantially pure.

In still yet another embodiment, the individual co-crystal forms of Compound (I) contains at least about 90 wt. %, preferably at least about 95 wt. %, and more preferably at least about 99 wt. % Compound (I), based on weight of the individual co-crystal forms of Compound (I).

In another embodiment, the Compound of formula (I) may have a mixture of the co-crystals described herein.

The present invention includes the use of the co-crystals of the compound of formula (I) for use in therapy.

The present invention is directed to the use of the co-crystals of the compound of formula (I) for the preparation of a medicament for the treatment or prophylaxis of a thromboembolic disorder.

In preparing a pharmaceutical composition, a form of the active ingredient is sought that has a balance of desired properties, such as, for example, dissolution rate, solubility, bioavailability, and/or storage stability. For example, a form of the active ingredient is sought having sufficient solubility, and bioavailability, and storage stability to prevent the sufficiently soluble and bioavailable form from converting during storage to another form having an undesirable solubility and/or bioavailability profile.

The present invention provides at least one co-crystal form of Compound (I) that surprisingly affords a balance of properties sought in a pharmaceutical composition. The present invention is also directed to other important aspects.

This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

The names used herein to characterize a specific form, e.g., "N-1" etc., are merely identifiers that are to be interpreted in accordance with the characterization information presented herein and are not to be limited so as to exclude any other substance possessing similar or identical physical and chemical characteristics.

The definitions set forth herein take precedence over definitions set forth in any patent, patent application, and/or patent application publication incorporated herein by reference.

All numbers expressing quantities of ingredients, weight percentages, temperatures, and so forth that are preceded by the word "about" are to be understood as only approximations so that slight variations above and below the stated number may be used to achieve substantially the same results as the stated number. Accordingly, unless indicated to the contrary, numerical parameters preceded by the word "about", or "substantially in accordance" are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

All measurements are subject to experimental error and are within the spirit of the invention.

As used herein, "co-crystal" means solid state, crystalline material that is composed of two or more molecules in the same crystal lattice which are in the neutral state, interact via nonionic interactions and are solids as individual components at room temperature.

As used herein, "polymorphs" refer to crystalline forms having the same chemical structure but different spatial arrangements of the molecules and/or ions forming the crystals.

As used herein "solvate" refers to a crystalline form of a molecule, atom, and/or ions that further comprises molecules of a solvent or solvents incorporated into the crystalline lattice structure. When the solvent is water, the form is referred to as a "hydrate". The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule or co-crystal of the compound of formula (I) within the crystalline lattice structure.

As used herein "amorphous" refers to a solid form of a molecule, atom, and/or ions that is not crystalline. An amorphous solid does not display a definitive X-ray diffraction pattern.

As used herein, "substantially pure," when used in reference to a co-crystal form, means a compound having a purity greater than 90 weight %, including greater than 90, 91, 92, 93, 94, 95, 96, 97, 98, and 99 weight %, and also including equal to about 100 weight % of the co-crystal of the Compound (I), based on the weight of the compound. The remaining material comprises other form(s) of the compound, and/or reaction impurities and/or processing impurities arising from its preparation. For example, a co-crystal form of Compound (I) may be deemed substantially pure in that it has a purity greater than 90 weight %, as measured by means that are at this time known and generally accepted in the art, where the remaining less than 10 weight % of material comprises other form(s) of Compound (I) and/or reaction impurities and/or processing impurities.

When dissolved, co-crystal forms of the compound of formula (I) loses its crystalline structure, and is therefore referred to as a solution of the compound of formula (I). All forms of the present invention, however, may be used for the preparation of liquid formulations in which the drug is dissolved or suspended. In addition, the co-crystal forms of the compound of formula (I) may be incorporated into solid formulations.

As used herein, an XRPD (x-ray powder diffraction) or PXRD (powder x-ray diffraction) pattern "comprising" or having a number of peaks selected from a specified group of peaks, is intended to include PXRD patterns having additional peaks that are not included in the specified group of peaks. For example, a PXRD pattern comprising at least one or more, four or more, five or more, or six or more, 20 values selected from: A, B, C, D, E, F, G, and H, is intended to include a PXRD pattern having: (a) at least one or more, four or more, five or more, six or more, 20 values selected from: A, B, C, D, E, F, G, and H; and (b) zero or more peaks that are not one of peaks A, B, C, D, E, F, G, and H.

As used herein, the term "DSC" refers to differential scanning calorimetry. The term "TGA" refers to thermogravimetric analysis. The term "IR" refers to infrared spectroscopy. The abbreviation "FT" stands for Fourier Transform.

The term "room temperature" generally means approximately 22° C., but may vary up or down by 7°C.

When the term "substantially in accordance" is used in relation to XRPD, or PXRD patterns, it is to be understood that measurement of the peak locations for a given crystalline form of the same compound will vary within a margin of error. It is also to be understood that the intensities of the peaks can vary between different PXRD scans of the same crystalline form of the same compound. The relative intensities of the different peaks are not meant to be limiting to a comparison of different PXRD scans.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In another embodiment, the therapeutically effective amount of the PAR4 compound is less than 5 mg/kg. In another embodiment, the therapeutically effective amount of the PAR4 compound is less than 1 mg/kg. In another embodiment, the dosage is 8 mg to 48 mg. Effective doses vary, as recognized by those skilled in the art, depending on route of administration and excipient usage.

The co-crystal forms are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The co-crystals of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Co-crystals of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate. Soft Gelatin Capsules A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isosmotic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the co-crystal of the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the co-crystalline forms of the compound (I) and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

As discussed above, compounds of the present invention, including the co-crystal forms of the compound of formula I can be administered orally, intravenously, or both.

EXAMPLES

Co-crystal forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of co-crystal forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, Chemical Engineering Science, 1971,26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be comilled or passed through a mesh screen to delump the product, if necessary.

The presence of more than one polymorph in a sample may be determined by techniques such as powder x-ray diffraction (PXRD) or by Raman or IR spectroscopy solid state nuclear magnetic resonance spectroscopy. For example, the presence of extra peaks in the comparison of an experimentally measured PXRD pattern with a simulated PXRD pattern may indicate more than one polymorph in the sample. The simulated PXRD may be calculated from single crystal x-ray data. see Smith, D. K., "A FORTRAN Program for Calculating X-Ray Powder Diffraction Patterns," Lawrence Radiation Laboratory, Livermore, California, UCRL-7196 (April 1963).

The co-crystal forms of the compound of formula (I) according to the invention may be characterized using various techniques, the operation of which are well known to those of ordinary skill in the art. The forms may be characterized and distinguished using single crystal x-ray diffraction, which is based on unit cell measurements of a single crystal of form at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, both run at the same analytical temperature, and measurements for the subject form characterized as a series of 2θ values (usually four or more).

Other means of characterizing the form may be used, such as solid state nuclear magnetic resonance (SSNMR), differential scanning calorimetry, thermogravimetric analysis and FT-Raman and FT-IR. These techniques may also be used in combination to characterize the subject form. In addition to the techniques specifically described herein, the presence of a particular crystalline form may be determined by other suitable analytical methods.

Example 1

4-(4-(((6-Methoxy-2-(2-methoxyimidazo[2,1-b][1,3,4] thiadiazol-6-yl)benzofuran-4-yl)oxy)methyl)thiazol-2-yl)-N,N-dimethylbenzamide: succinic acid co-crystal (1:0.5)

To a 250 mL glass reactor were added the compound of formula (I) as a free form (2 g, 3.561 mmol), dichloromethane (100 mL) and methanol (20 mL). The reaction mass was heated to 39°C, until full dissolution. Succinic acid (0.45 g, 3.8 mmol) was then added in one portion. After 3 days, 50 mL of the solution mass was distilled off, until a slurry forms. Ethyl acetate (70 mL) was added. The volatiles were removed to dryness and ethyl acetate (100 mL) was charged to the reaction mixture and the reaction mass was stirred for 12 h. The resulting slurry was then filtered off and the resulting solid was washed with ethyl acetate (10 mL). The solid was dried in a vacuum oven for 24 h (30 mmHg, 50° C.) to give the succinic acid co-crystal of the compound of formula (I). The product was obtained as a white solid (1.8 g, 41% yield), with a purity of 99.4% by HPLC. 1H NMR (400 MHZ, DMSO-d6) d 8.37 (s, 2H), 8.03 (s, 2H), 8.01 (s, 2H), 7.94 (s, 2H), 7.54 (d, J=7.8 Hz, 4H), 7.03 (s, 2H), 6.85 (dd, J=1.8, 0.8 Hz, 2H), 6.65 (d, J=1.8 Hz, 2H), 5.39 (s, 4H), 4.20 (s, 6H), 3.90-3.77 (m, 6H), 3.31 (s, 5H), 3.00 (br s, 6H), 2.94 (br s, 6H), 2.43-2.41 (m, 4H).

The succinic acid co-crystal has a stoichiometry of one molecule of the compound of formula (I) to 0.5 molecules of succinic acid, or a hemisuccinate of the compound of formula (I).

Figure 2:
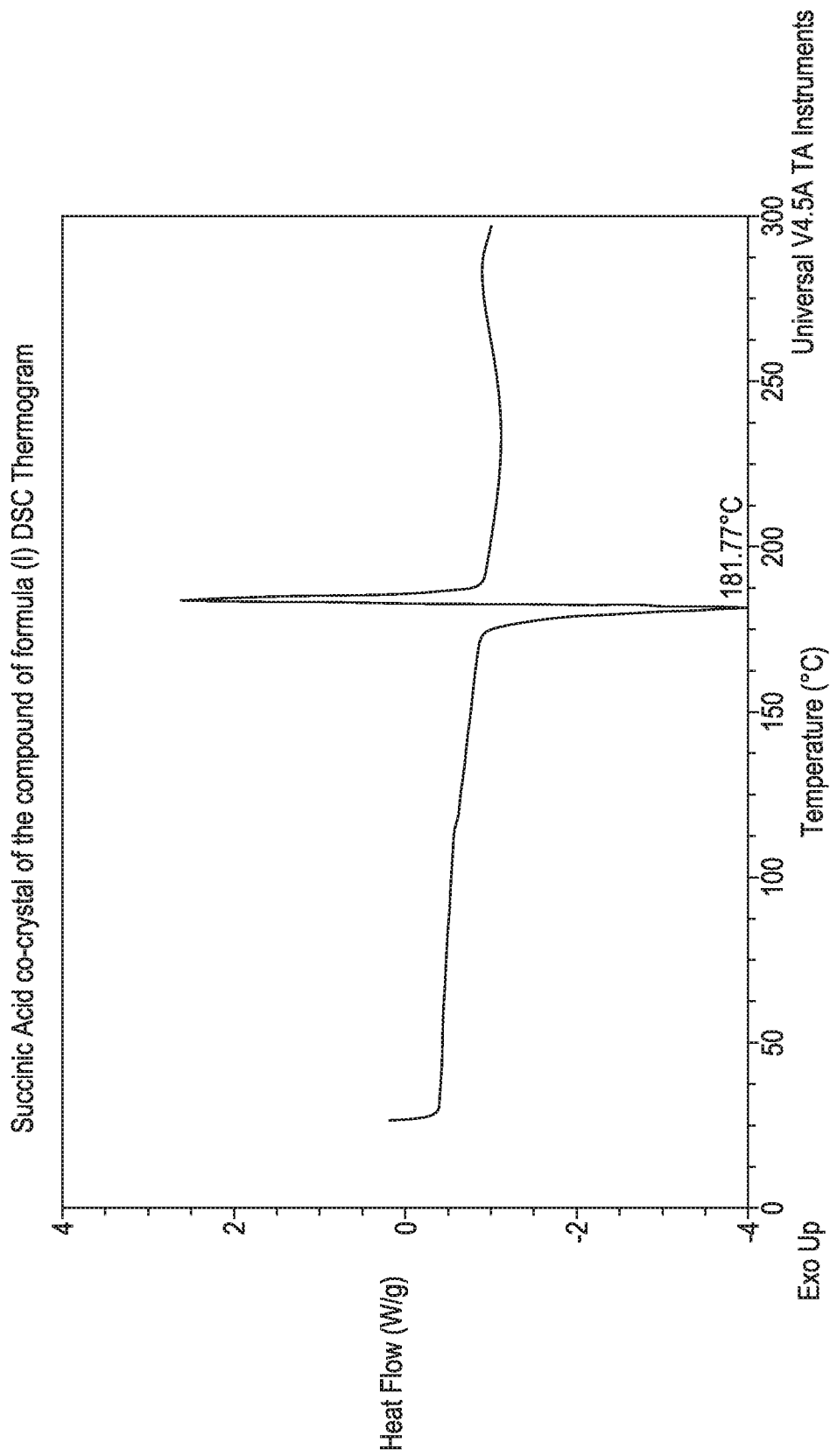
FIG. 2 shows the DSC of the succinic acid co-crystal of the compound of formula (I).
Figure 3:
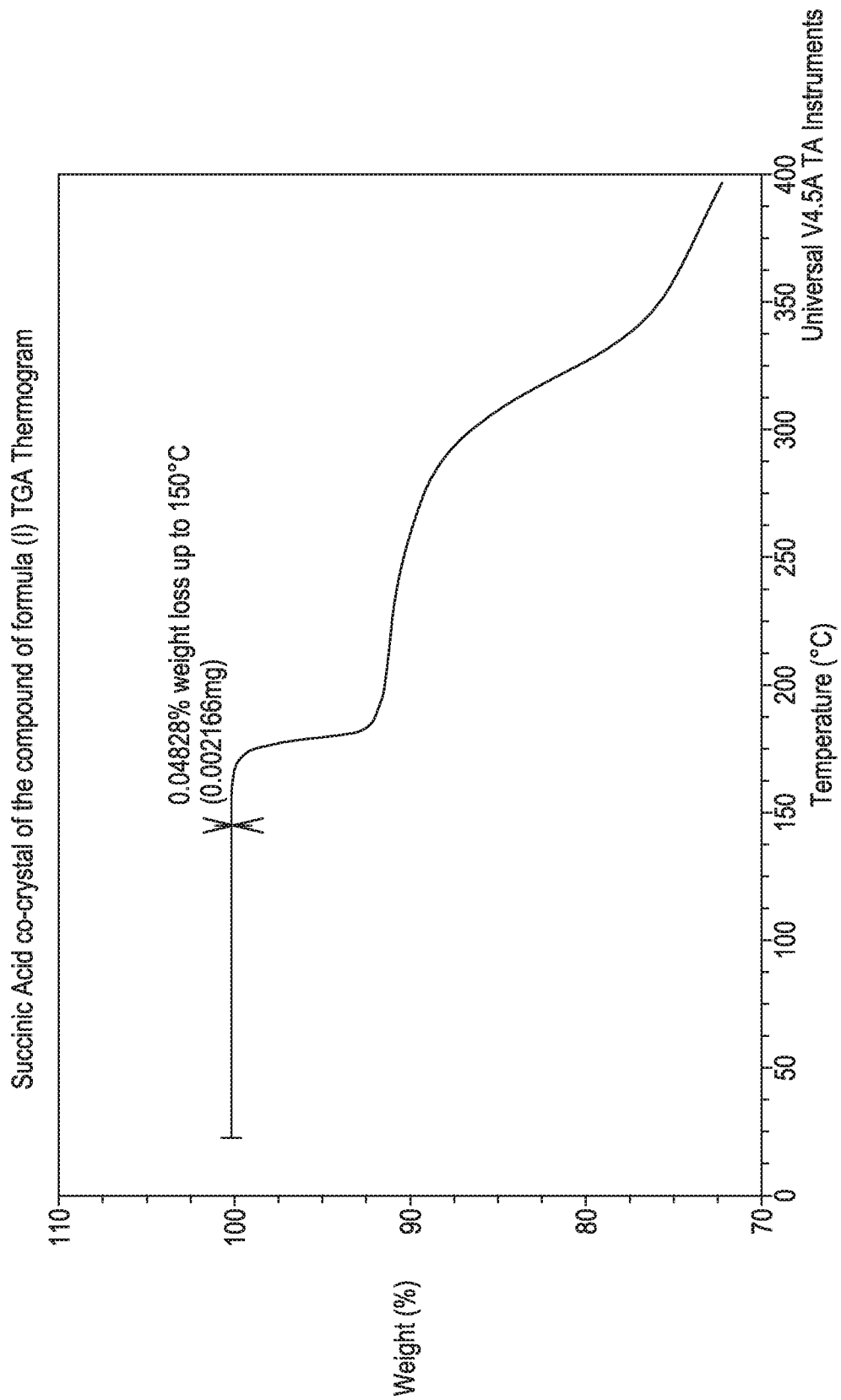
FIG. 3 shows the TGA of the succinic acid co-crystal of the compound of formula (I).

The succinic acid co-crystal of the compound of formula (I) gave the PXRD pattern shown in FIG. 1, the Differential Scanning calorimeter (DSC) shown in FIG. 2, and the thermogravimetric analysis (TGA) shown in FIG. 3.

The PXRD of the succinic acid co-crystal of the compound of formula (I) has selected 2θ peaks at 4.5, 9.5, 14.6, 16.3, 17.6, 21.4, 22.4 and 25.9, (all peaks at degrees 2θ±0.2). The PXRD was obtained at room temperature, and the diffraction peak positions (degrees 2θ±0.2), based on a high quality pattern collected with a diffractometer (CuKα) with a spinning capillary with 2θ calibrated with a NIST other suitable standard.

The succinic acid co-crystal is also characterized by a PXRD having at least one or more, or 4 or more, 2θ values selected from 4.5±0.2, 9.5±0.2, 14.6±0.2, 16.3±0.2, 17.6±0.2, 21.4±0.2, 22.4±0.2, and 25.9±0.2.

The succinic acid co-crystal is also characterized by a PXRD having 4 or more 2θ values selected from 4.510.2, 9.510.2, 14.610.2, 16.310.2, 17.610.2, and 25.910.2.

A single crystal X-ray of the succinic acid co-crystal of the compound of formula (I) was obtained and produced the following results:

| | | |
|---|---|---|
| Temperature | room temperature | |
| Wavelength | 1.54178 Å | |
| Crystal system, space group | Triclinic, P-1 | |
| Unit cell dimensions | a = 7.5209(7) Å | alpha = 103.201(4)° |
| | b = 9.6255(6) Å | beta = 91.833(5)° |
| | c = 20.089(1) Å | gamma = 97.501(6)° |
| Volume | 1400.8(2) Å$^3$ | |
| Calculated density | 1.471 g/cm$^3$ | |
| formula units per unit cell | 2 | |

The atomic coordinates for the single crystal X-ray for the succinic acid co-crystal are shown in Table 1.

TABLE 1

Atomic Coordinates of Succinate Acid Co-crystal

| Atom | X | Y | Z |
|---|---|---|---|
| S1 | 1.3819 | 1.0196 | 0.3789 |
| S2 | 0.7569 | 0.4869 | 0.6965 |
| N1 | 1.2580 | 1.0724 | 0.5123 |
| N2 | 1.4110 | 1.2469 | 0.4731 |
| N3 | 1.5027 | 1.2961 | 0.4223 |

TABLE 1-continued

Atomic Coordinates of Succinate Acid Co-crystal

| Atom | X | Y | Z |
|---|---|---|---|
| N4 | 0.7484 | 0.6470 | 0.8167 |
| N5 | 0.3134 | 0.0672 | 0.9555 |
| O1 | 1.2217 | 1.3320 | 0.6754 |
| O2 | 0.9340 | 0.9577 | 0.7554 |
| O3 | 1.0570 | 1.4185 | 0.9115 |
| O4 | 1.5673 | 1.1838 | 0.3121 |
| O5 | 0.4178 | −0.0757 | 0.8652 |
| C1 | 1.2781 | 1.2022 | 0.5618 |
| C2 | 1.3725 | 1.3113 | 0.5387 |
| C3 | 1.3401 | 1.1067 | 0.4604 |
| C4 | 1.4962 | 1.1865 | 0.3716 |
| C5 | 1.2023 | 1.2016 | 0.6267 |
| C6 | 1.1440 | 1.3005 | 0.7326 |
| C7 | 1.0753 | 1.1557 | 0.7190 |
| C8 | 1.1150 | 1.0935 | 0.6504 |
| C9 | 1.1432 | 1.3976 | 0.7948 |
| C10 | 1.0669 | 1.3400 | 0.8459 |
| C11 | 0.9935 | 1.1945 | 0.8352 |
| C12 | 0.9972 | 1.1015 | 0.7722 |
| C13 | 0.8653 | 0.8919 | 0.8068 |
| C14 | 0.8180 | 0.7344 | 0.7755 |
| C15 | 0.8322 | 0.6670 | 0.7094 |
| C16 | 0.7090 | 0.5131 | 0.7815 |
| C17 | 0.6313 | 0.3948 | 0.8115 |
| C18 | 0.5558 | 0.2622 | 0.7706 |
| C19 | 0.4807 | 0.1528 | 0.7993 |
| C20 | 0.4775 | 0.1732 | 0.8699 |
| C21 | 0.5576 | 0.3044 | 0.9107 |
| C22 | 0.6330 | 0.4135 | 0.8823 |
| C23 | 0.3986 | 0.0463 | 0.8965 |
| C24 | 0.2564 | 0.1992 | 0.9920 |
| C25 | 0.2529 | -0.0588 | 0.9814 |
| C26 | 1.1240 | 1.5674 | 0.9257 |
| C27 | 1.6643 | 1.3165 | 0.3026 |
| C1A | 0.9198 | 0.2959 | 0.4847 |
| C2A | 0.9469 | 0.4532 | 0.5200 |
| O1A | 0.8302 | 0.2168 | 0.52.17 |
| O2A | 0.9747 | 0.2484 | 0.4300 |
| H2 | 1.4037 | 1.4072 | 0.5620 |
| H8 | 1.0862 | 0.9976 | 0.6269 |
| H9 | 1.1903 | 1.4944 | 0.8017 |
| H11 | 0.9418 | 1.1606 | 0.8709 |
| H13A | 0.7596 | 0.9324 | 0.8240 |
| H13B | 0.9547 | 0.9076 | 0.8446 |
| H15 | 0.8764 | 0.7121 | 0.6758 |
| H18 | 0.5560 | 0.2468 | 0.7232 |
| H19 | 0.4316 | 0.0645 | 0.7711 |
| H21 | 0.5601 | 0.3188 | 0.9581 |
| H22 | 0.6856 | 0.5006 | 0.9107 |
| H24A | 0.3231 | 0.2325 | 1.0355 |
| H24B | 0.1305 | 0.1822 | 0.9990 |
| H24C | 0.2776 | 0.2708 | 0.9658 |
| H25A | 0.1387 | −0.1048 | 0.9589 |
| H25B | 0.2408 | −0.0299 | 1.0299 |
| H25C | 0.3390 | −0.1251 | 0.9726 |
| H26A | 1.2475 | 1.5798 | 0.9149 |
| H26B | 1.1148 | 1.6097 | 0.9734 |
| H26C | 1.0548 | 1.6137 | 0.8985 |
| H27A | 1.5917 | 1.3924 | 0.3147 |
| H27B | 1.6922 | 1.3050 | 0.2556 |
| H27C | 1.7737 | 1.3406 | 0.3313 |
| H2A1 | 1.0025 | 0.4686 | 0.5651 |
| H1A1 | 0.8341 | 0.4795 | 0.5272 |
| H1A | 0.8025 | 0.1272 | 0.4991 |

The DSC of the succinic acid co-crystal showed a variable endotherm at about 182° C., which represented a melt with decomposition. The TGA of the succinic acid co-crystal showed negligible weight loss up to 150° ° C.

The FT-IR and FT-Raman are shown in FIGS. 4 and 5 respectively and showed characteristic peaks in the range from 1700 to 3500 cm$^{-1}$.

The FT-Raman spectrum for the succinic acid co-crystal has characteristic peaks at 975.3, 1185.0, 1242.9, 1455.6, and 3104.4 cm$^{-1}$ (+0.3 cm$^{-1}$).

The FT-IR spectrum for the succinic acid co-crystal has characteristic peaks at 1627.9, 1704.4, and 3102.1 cm$^{-1}$ (+0.4 cm$^{-1}$).

Example 2

4-(4-(((6-Methoxy-2-(2-methoxyimidazo[2,1-b][1,3,4] thiadiazol-6-yl)benzofuran-4-yl)oxy)methyl)thiazol-2-yl)-N,N-dimethylbenzamide: citric acid co-crystal (1:1), form N-1.

A mixture of 4-(4-(((6-Methoxy-2-(2-methoxyimidazo[2, 1-b][1,3,4]thiadiazol-6-yl)benzofuran-4-yl)oxy)methyl)thi-azol-2-yl)-N,N-dimethylbenzamide (6.1 g, 11 mmol, 1.0 eq) and citric acid (3.3 g, 18 mmol, 1.6 eq) in ethyl acetate (210 mL) was heated to 76° C. for 10 h and then slowly cool to room temperature and allowed to stir for 16 h. The slurry was filtered and washed with EtOAc (80 mL) followed by drying of the cake under vacuum in the oven at 55° C. for 1 days to give 8.0 g (98% yield) of the N-1 form of the citric acid co-crystal as a white solid.

Alternative Procedure

To citric acid (222.5 g, 1.16 mol, 1.3 eq) was added EtOAc (17 L) and heated to 55° C. for 2 h to give a clear solution. 4-(4-(((6-Methoxy-2-(2-methoxyimidazo[2,1-b][1, 3,4]thiadiazol-6-yl)benzofuran-4-yl)oxy)methyl)thiazol-2-yl)-N,N-dimethylbenzamide (500.00 g, 0.89 mol, 1.0 eq) was added followed by EtOAc (1L). The mixture was heated to 76° C. over 1 h. 4-(4-(((6-Methoxy-2-(2-methoxyimidazo [2,1-b][1,3,4]thiadiazol-6-yl)benzofuran-4-yl)oxy)methyl) thiazol-2-yl)-N,N-dimethylbenzamide citric acid co-crystal (1.0 g, 0.2% wt) in EtOAc (15 mL) was added as seeds. The mixture was heated for an additional 30 min and then slowly cooled to room temperature for 2 h and allowed to stir for 5 h. The slurry was filtered and washed twice with EtOAc (3 L) followed by drying of the cake under vacuum in the oven at 50° C. for 3 days to give 663.7 g (99% yield) in 99.8AP purity of the N-1 form of the citric acid co-crystal as a white solid.

The N-1 form of the citric acid co-crystal of the compound of formula (I) has a stoichiometry of 1 molecule of the compound of formula (I) for every molecule of citric acid (1:1).

Figure 7:
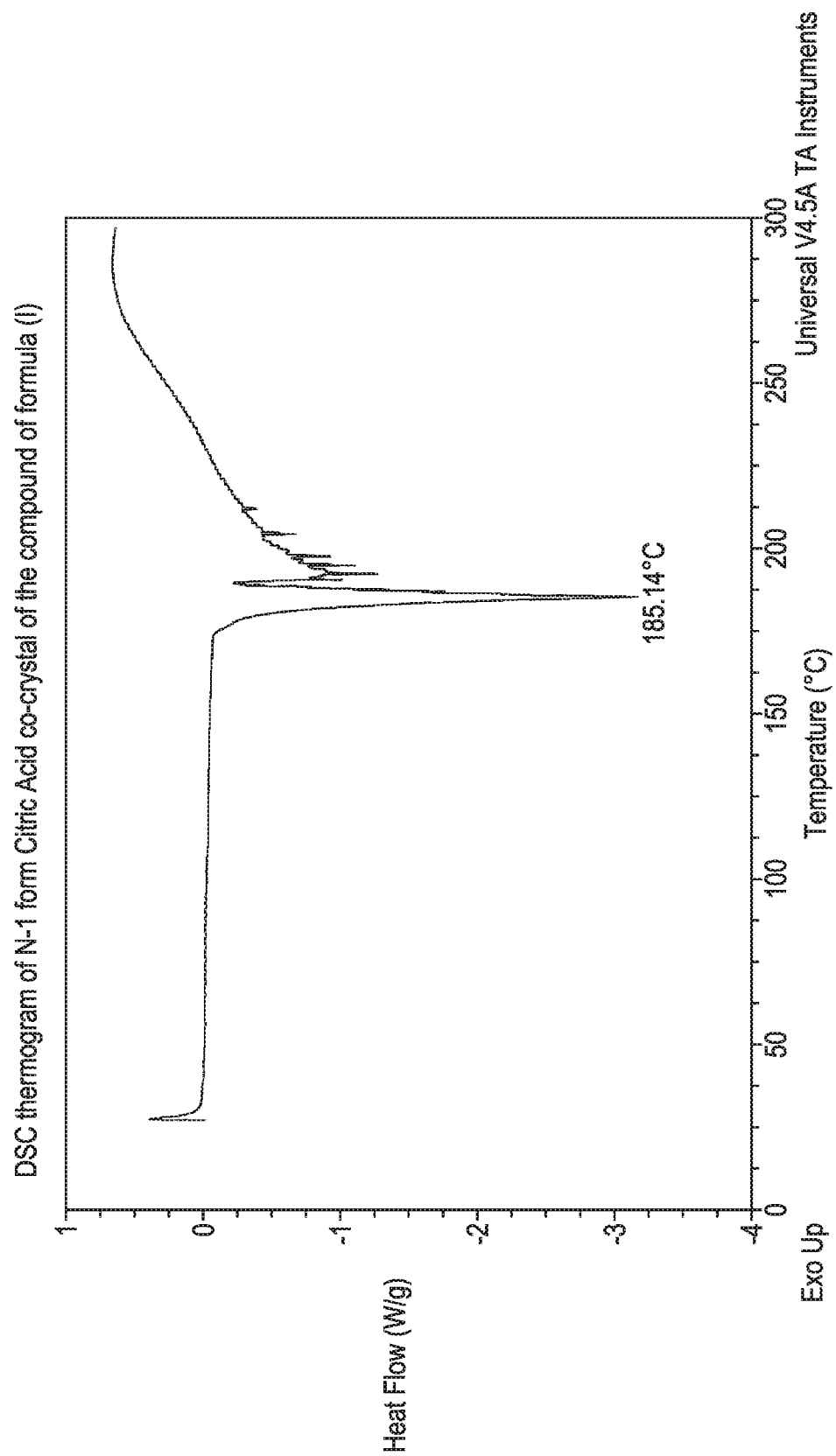
FIG. 7 shows the DSC of the N-1 form of the citric acid co-crystal of the compound of formula (I).
Figure 8:
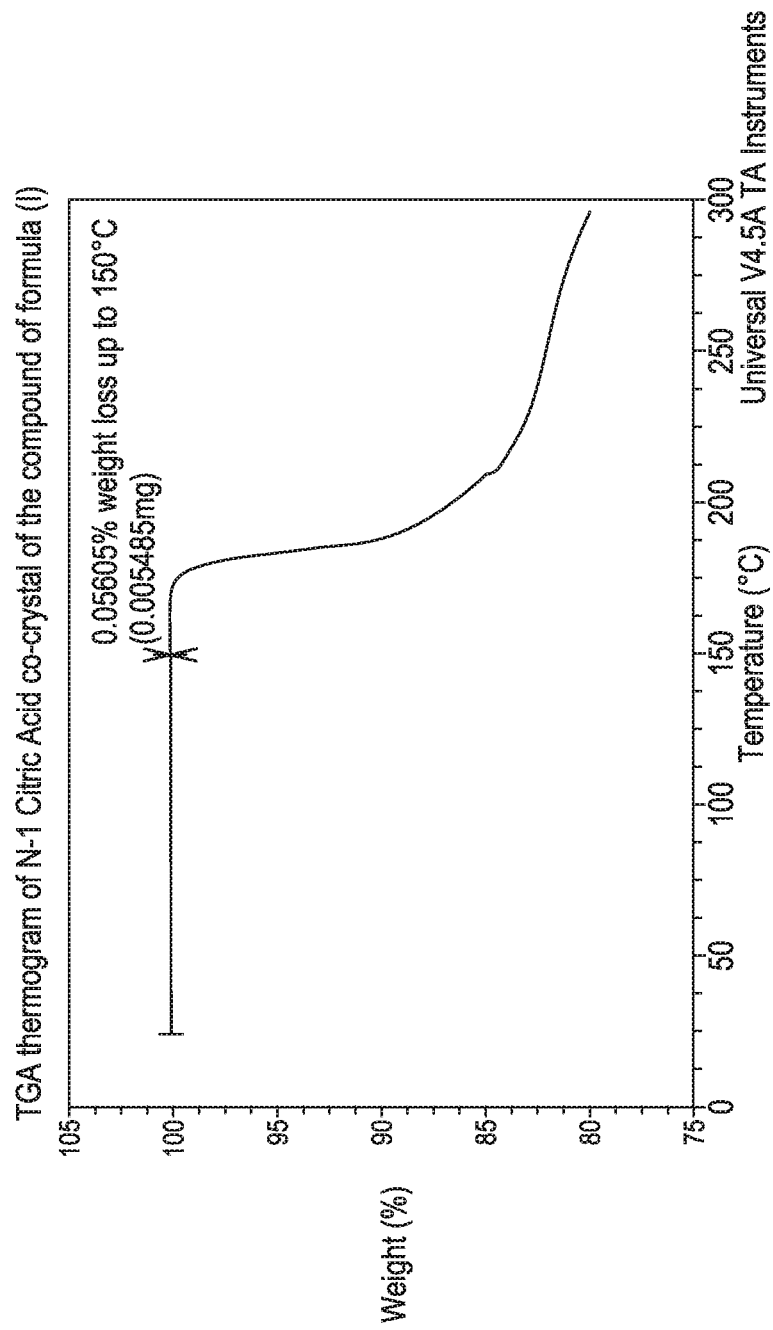
FIG. 8 shows the TGA of the N-1 form of the citric acid co-crystal of the compound of formula (I).

The N-1 Form of the citric acid co-crystal of the compound of formula (I) gave the PXRD pattern shown in FIG. 6, the DSC shown in FIG. 7, and the TGA shown in FIG. 8.

The form N-1 of the citric acid co-crystal of the compound of formula (I) has a PXRD with select 2θ peaks at 6.4, 12.7. 14.4, 17.1, 23.9, 25.0, and 26.6, (all peaks at degrees 2θ±0.2). The PXRD was obtained at room temperature, and the diffraction peak positions (degrees 2θ±0.2), are based on a high quality pattern collected with a diffractometer (CuKα) with a spinning capillary with 2θ calibrated with a NIST or other suitable standard.

The form N-1 of the citric acid co-crystal of the compound of formula (I) has a PXRD with select 2θ peaks at 6.4, 12.7. 14.4, and 26.6, (all peaks at degrees 2θ±0.2). The PXRD was obtained at room temperature, and the diffraction peak positions (degrees 2θ±0.2), are based on a high quality pattern collected with a diffractometer (CuKα) with a spinning capillary with 2θ calibrated with a NIST or other suitable standard.

The N-1 form of the citric acid co-crystal is also characterized by a PXRD having one or more, or 4 or more, 20 values selected from 6.4±0.2, 12.7±0.2. 14.4±0.2, 17.1±0.2, 23.9±0.2, 25.0±0.2, and 26.6±0.2.

The N-1 form of the citric acid co-crystal is also characterized by a PXRD having 4 or more 2θ values selected from 6.4±0.2, 12.7±0.2. 14.4±0.2, and 26.6±0.2.

A single crystal X-ray of the N-1 form of the citric acid co-crystal of the compound of formula (I) was obtained and produced the following results:

Temperature room temperature
Wavelength 1.54178 Å
Crystal system, space group Triclinic, P-1
Unit cell dimensions a=10.293(1) Å alpha=94.005(7) °
b=12.270(2) Å beta=98.188(7) °
c=13.937(2) Å gamma=98.166(8) °
Volume 1717.1(4) Å$^3$
Calculated density 1.458 g/cm$^3$
formula units per unit cell 2

The atomic coordinates for the single crystal X-ray for the N-1 form of the citric acid co-crystal are shown in Table 3.

TABLE 3

| Atom | X | Y | Z |
|---|---|---|---|
| S1 | 0.4512 | 0.2863 | 0.0346 |
| S2 | −0.1441 | 0.8204 | 0.2062 |
| O1 | 0.2395 | 0.6123 | −0.2546 |
| O2 | −0.0047 | 0.8097 | −0.0771 |
| O3 | 0.0104 | 0.8900 | −0.4059 |
| O4 | 0.6135 | 0.1678 | −0.0342 |
| O5 | −0.6703 | 1.0474 | 0.4089 |
| N1 | 0.3138 | 0.4519 | −0.0458 |
| N2 | 0.4482 | 0.3695 | −0.1267 |
| N3 | 0.5346 | 0.2939 | −0.1355 |
| N4 | −0.2186 | 0.9346 | 0.0679 |
| N5 | −0.5866 | 1.2223 | 0.3927 |
| C1 | 0.3986 | 0.4421 | −0.1876 |
| C2 | 0.3948 | 0.3784 | −0.0436 |
| C3 | 0.3156 | 0.4921 | −0.1366 |
| C4 | 0.5418 | 0.2462 | −0.0559 |
| C5 | 0.2397 | 0.5788 | −0.1613 |
| C6 | 0.1695 | 0.6386 | −0.1096 |
| C7 | 0.1205 | 0.7163 | −0.1722 |
| C8 | 0.1643 | 0.6967 | −0.2600 |
| C9 | 0.1331 | 0.7493 | −0.3426 |
| C10 | 0.0506 | 0.8285 | −0.3329 |
| C11 | 0.0021 | 0.8511 | −0.2453 |
| C12 | 0.0364 | 0.7957 | −0.1658 |
| C13 | 0.7000 | 0.1415 | −0.1012 |
| C14 | 0.0519 | 0.8679 | −0.4977 |
| C15 | −0.1056 | 0.8751 | −0.0674 |
| C16 | −0.1332 | 0.8696 | 0.0352 |
| C17 | −0.0843 | 0.8031 | 0.0993 |
| C18 | −0.2338 | 0.9175 | 0.1577 |
| C19 | −0.3212 | 0.9714 | 0.2133 |
| C20 | −0.3341 | 0.9473 | 0.3081 |
| C21 | −0.4196 | 0.9953 | 0.3589 |
| C22 | −0.4923 | 1.0709 | 0.3180 |
| C23 | −0.4797 | 1.0963 | 0.2246 |
| C24 | −0.3949 | 1.0467 | 0.1727 |
| C25 | −0.5889 | 1.1146 | 0.3758 |
| C26 | −0.4867 | 1.3077 | 0.3657 |
| C27 | −0.6794 | 1.2612 | 0.4522 |
| O1A | 0.3438 | 0.5445 | 0.3654 |
| O2A | 0.0121 | 0.5695 | 0.3989 |
| O3A | 0.1700 | 0.4982 | 0.4882 |
| O4A | 0.1933 | 0.5023 | 0.1043 |
| O5A | 0.2960 | 0.3715 | 0.1681 |
| O6A | 0.2312 | 0.8560 | 0.3198 |
| O7A | 0.3254 | 0.7611 | 0.4332 |
| C1A | 0.2109 | 0.5546 | 0.3320 |
| C2A | 0.1252 | 0.5423 | 0.4139 |
| C3A | 0.2224 | 0.4387 | 0.1736 |
| C4A | 0.1510 | 0.4546 | 0.2594 |
| C5A | 0.2605 | 0.7644 | 0.3553 |
| C6A | 0.2014 | 0.6641 | 0.2873 |
| H1 | 0.4173 | 0.4544 | −0.2496 |

TABLE 3-continued

| Atom | X | Y | Z |
|---|---|---|---|
| H6 | 0.1554 | 0.6310 | −0.0458 |
| H9 | 0.1647 | 0.7329 | −0.4003 |
| H11 | −0.0537 | 0.9041 | −0.2414 |
| H13A | 0.6484 | 0.1157 | −0.1636 |
| H13B | 0.7482 | 0.0848 | −0.0777 |
| H13C | 0.7614 | 0.2064 | −0.1072 |
| H14A | 0.1468 | 0.8857 | −0.4910 |
| H14B | 0.0116 | 0.9120 | −0.5442 |
| H14C | 0.0252 | 0.7910 | −0.5197 |
| H15A | −0.1850 | 0.8463 | −0.1133 |
| H15B | −0.0760 | 0.9508 | −0.0793 |
| H17 | −0.0259 | 0.7544 | 0.0869 |
| H20 | −0.2839 | 0.8978 | 0.3374 |
| H21 | −0.4284 | 0.9766 | 0.4215 |
| H23 | −0.5284 | 1.1471 | 0.1961 |
| H24 | −0.3877 | 1.0645 | 0.1097 |
| H26A | −0.4142 | 1.2742 | 0.3470 |
| H26B | −0.4545 | 1.3616 | 0.4203 |
| H26C | −0.5262 | 1.3431 | 0.3121 |
| H27A | −0.7613 | 1.2107 | 0.4406 |
| H27B | −0.6959 | 1.3331 | 0.4355 |
| H27C | −0.6419 | 1.2655 | 0.5198 |
| H1A | 0.3765 | 0.5958 | 0.4066 |
| H3A | 0.1166 | 0.4960 | 0.5267 |
| H4A | 0.2349 | 0.4901 | 0.0597 |
| H6A | 0.2650 | 0.9091 | 0.3587 |
| H4A1 | 0.1492 | 0.3885 | 0.2939 |
| H4A2 | 0.0597 | 0.4618 | 0.2352 |
| H6A1 | 0.2461 | 0.6648 | 0.2306 |
| H6A2 | 0.1086 | 0.6683 | 0.2655 |

The DSC of the N-1 form of the citric acid co-crystal showed a variable endotherm at about 185-190° C., which represented a melt with decomposition. The TGA of the N-1 form of the citric acid co-crystal showed negligible weight loss up to 150° C.

The C-13 solid state NMR (C-13 SSNMR) of the citric acid co-crystal demonstrated peaks as shown in Table 4. The C-13 SSNMR is consistent with Z'=2.

TABLE 4

| N-1 citric acid co-crystal C-13 Chemical Shifts | |
|---|---|
| (ppm) | (ppm) |
| 182 | 126.3 |
| 175.5 | 122.9 |
| 172.3 | 113 |
| 171.1 | 109.2 |
| 167 | 99 |
| 160.1 | 94.9 |
| 156 | 86.7 |
| 154.1 | 74.7 |
| 151.4 | 65.5 |
| 148.2 | 60.4 |
| 141.3 | 55.8 |
| 135.9 | 42.9 |
| 133.7 | 40.9 |
| 131.2 | 40 |
| | 35.2 |

The IR and Raman spectroscopy of the N-1 form of the citric acid co-crystal demonstrated peaks as shown in FIGS. 9 and 11. The spectra demonstrated characteristic peaks shown in the range from 1700 to 3500 cm$^{-1}$.

The FT-Raman spectrum for the N-1 citric acid co-crystal has characteristic peaks at 755.3, 807.7, 982.1, 1191.2, 1367.8, 1450.6, and 2978.9 cm$^{-1}$ (±0.3 cm$^{-1}$).

The FT-IR spectrum for the N-1 citric acid co-crystal has characteristic peaks at 1585.7, 1725.9, and 3150.5 cm$^{-1}$ (±0.4 cm$^{-1}$).

Example 3

4-(4-(((6-Methoxy-2-(2-methoxyimidazo[2,1-b][1,3,4]thiadiazol-6-yl)benzofuran-4-yl)oxy)methyl)thiazol-2-yl)-N,N-dimethylbenzamide: citric acid co-crystal (1:1), form N-2.

A mixture of 4-(4-(((6-Methoxy-2-(2-methoxyimidazo[2,1-b][1,3,4]thiadiazol-6-yl)benzofuran-4-yl)oxy)methyl)thiazol-2-yl)-N,N-dimethylbenzamide (5.00 g, 8.9 mmol, 1 eq) and citric acid (2.50 g, 13.4 mmol, 1.5 eq) in 200 mL EtOAc was heated to 74° C. for 18 h. The mixture was slowly cool to room temperature and allowed to stir for 3 h. The slurry was filtered and washed twice with EtOAc (20 mL) followed by drying of the cake under vacuum in the oven at 55° C. for 1 day to give 6.5 g (97% yield) of form N-2 of the citric acid co-crystal as a needle white solid.

The N-2 form of the citric acid co-crystal of the compound of formula (I) contains 1 molecule of the compound of formula (I) for every molecule of citric acid (1:1).

Figure 13:
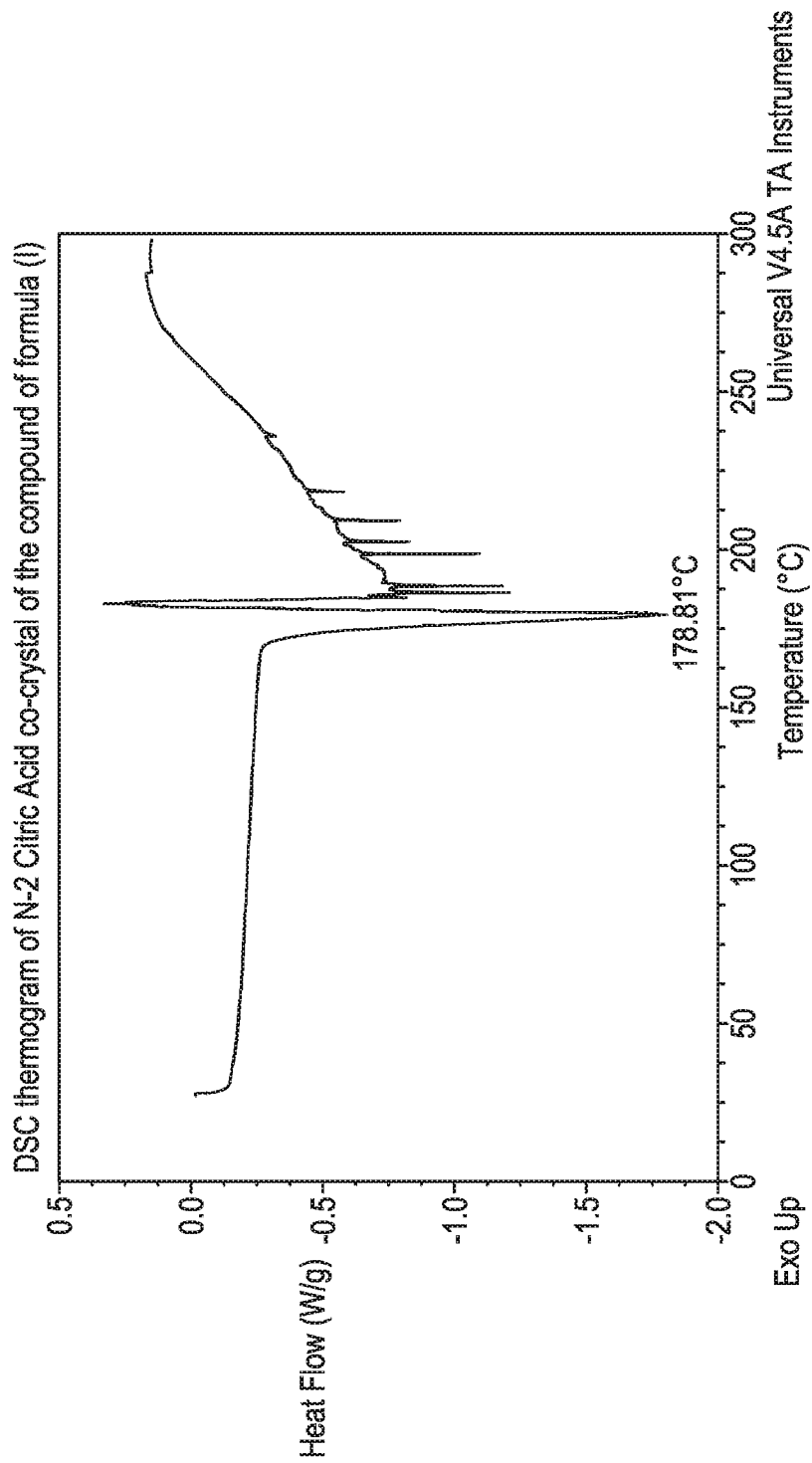
FIG. 13 shows the DSC of the N-2 form of the citric acid co-crystal of the compound of formula (I).
Figure 14:
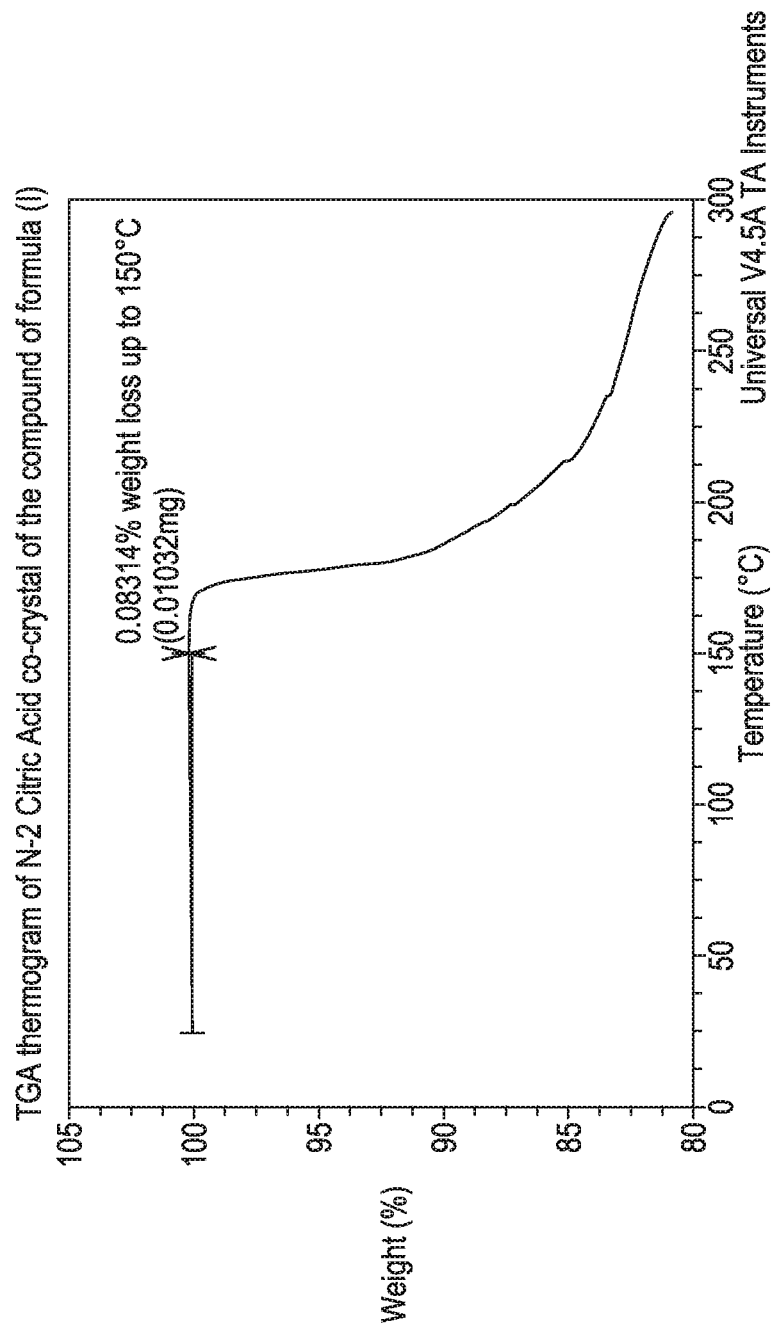
FIG. 14 shows the TGA of the N-2 form of the citric acid co-crystal of the compound of formula (I).

The N-2 Form of the citric acid co-crystal of the compound of formula (I) gave the PXRD pattern shown in FIG. 12, the DSC shown in FIG. 13, and the TGA shown in FIG. 14.

The N-2 form of the citric acid co-crystal of the compound of formula (I) has a PXRD with select 2θ peaks at 4.6, 14.6, 16.4, 21.0, and 25.2, (all peaks at degrees 2θ±0.2). The PXRD was obtained at room temperature, and the diffraction peak positions (degrees 2θ±0.2, based on a high quality pattern collected with a diffractometer (CuKα) with a spinning capillary with 2θ calibrated with a NIST suitable standard.

The N-2 form of the citric acid co-crystal of the compound of formula (I) has a PXRD with select 2θ peaks at 4.6, 5.5, 8.4, 11.3, 14.6, 16.4, 21.0, 24.2 and 25.2, (all peaks at degrees 2θ±0.2). The PXRD was obtained at room temperature, and the diffraction peak positions (degrees 2θ±0.2), based on a high quality pattern collected with a diffractometer (CuKα) with a spinning capillary with 2θ calibrated with a NIST suitable standard.

The N-2 form of the citric acid co-crystal is also characterized by a PXRD having one or more, or 4 or more, 2θ values selected from 4.6±0.2, 5.5±0.2, 8.4±0.2, 11.3±0.2, 14.6±0.2, 16.4±0.2, 21.0±0.2, 24.2±0.2, and 25.2±0.2.

The N-2 form of the citric acid co-crystal is also characterized by a PXRD having 4 or more 2θ values selected from 4.6±0.2, 14.6±0.2, 16.4±0.2, 21.0±0.2, and 25.2±0.2.

A single crystal X-ray of the N-2 form of the citric acid co-crystal of the compound of formula (I) was obtained and produced the following results:

| | |
|---|---|
| Temperature | room temperature |
| Wavelength | 1.54178 Å |
| Crystal system, space group | Triclinic, P-1 |
| Unit cell dimensions | a = 10.4364(4) Å   alpha = 111.270(2)° |
| | b = 17.8418(8) Å   beta = 92.635(3)° |
| | c = 20.5491(9) Å   gamma = 101.641(3)° |
| Volume | 3462.4(3) Å³ |
| Calculated density | 1.446 g/cm³ |
| Molecules per unit cell | 4 |

The atomic coordinates for the single crystal X-ray for the N-2 form of the citric acid co-crystal are shown in Table 5.

TABLE 5

| Atom | X | Y | Z |
|---|---|---|---|
| S1A | 1.3310 | 0.7354 | 0.5021 |
| S2A | 0.4560 | 0.7843 | 0.6928 |
| O1A | 1.1165 | 1.0559 | 0.5766 |
| O2A | 0.7224 | 0.9856 | 0.6550 |
| O3A | 0.8398 | 1.2529 | 0.6454 |
| O4A | 1.5651 | 0.7506 | 0.4617 |
| O5A | −0.2774 | 0.7204 | 0.7003 |
| N1A | 1.3618 | 0.8842 | 0.5136 |
| N2A | 1.1688 | 0.8494 | 0.5467 |
| N3A | 1.4787 | 0.8671 | 0.4896 |
| N4A | 0.3948 | 0.9154 | 0.6924 |
| N5A | −0.2089 | 0.7523 | 0.8134 |
| C1A | 0.9221 | 1.0276 | 0.6170 |
| C2A | 0.9786 | 0.9572 | 0.6007 |
| C3A | 1.0931 | 0.9768 | 0.5770 |
| C4A | 1.0087 | 1.0859 | 0.6016 |
| C5A | 0.9913 | 1.1636 | 0.6097 |
| C6A | 0.8738 | 1.1794 | 0.6341 |
| C7A | 0.7816 | 1.1219 | 0.6492 |
| C8A | 0.8043 | 1.0462 | 0.6412 |
| C9A | 1.1929 | 0.9309 | 0.5519 |
| C10A | 1.2734 | 0.8247 | 0.5236 |
| C11A | 1.3118 | 0.9534 | 0.5317 |
| C12A | 1.4725 | 0.7921 | 0.4827 |
| C13A | 0.9356 | 1.3167 | 0.6383 |
| C14A | 1.6822 | 0.7953 | 0.4481 |
| C15A | 0.5982 | 0.9985 | 0.6749 |
| C16A | 0.5248 | 0.9223 | 0.6829 |
| H26A | −0.3902 | 0.7701 | 0.8231 |
| H26B | −0.3436 | 0.7299 | 0.8735 |
| H26C | −0.3865 | 0.6764 | 0.7931 |
| H27A | −0.0209 | 0.7996 | 0.8582 |
| H27B | −0.0998 | 0.7389 | 0.8895 |
| H27C | −0.1222 | 0.8286 | 0.9104 |
| S1B | 0.5594 | 0.5998 | 1.2742 |
| S2B | 1.1726 | 0.5790 | 0.7956 |
| N1B | 0.4242 | 0.4780 | 1.1705 |
| N2B | 0.6072 | 0.5252 | 1.1322 |
| N3B | 0.3447 | 0.4793 | 1.2218 |
| N4B | 1.0939 | 0.6095 | 0.9156 |
| N5B | 1.6697 | 0.9689 | 1.0605 |
| O1B | 0.4772 | 0.3577 | 0.9610 |
| O2B | 0.8449 | 0.4158 | 0.8440 |
| O3B | 0.5007 | 0.1896 | 0.7202 |
| O4B | 0.3617 | 0.5617 | 1.3404 |
| O5B | 1.6767 | 0.9384 | 0.9467 |
| C1B | 0.6566 | 0.3891 | 0.9088 |
| C2B | 0.5337 | 0.3352 | 0.9001 |
| C3B | 0.5687 | 0.4260 | 1.0083 |
| C4B | 0.6747 | 0.4474 | 0.9810 |
| C5B | 0.7250 | 0.3723 | 0.8487 |
| C6B | 0.6660 | 0.3025 | 0.7888 |
| C7B | 0.5460 | 0.2540 | 0.7840 |
| C8B | 0.4736 | 0.2684 | 0.8405 |
| C9B | 0.5265 | 0.4576 | 1.0792 |
| C10B | 0.5405 | 0.5346 | 1.1860 |
| C11B | 0.4143 | 0.4270 | 1.0997 |
| C12B | 0.4074 | 0.5408 | 1.2783 |
| C13B | 0.3756 | 0.1385 | 0.7133 |
| C14B | 0.2397 | 0.5088 | 1.3436 |
| C15B | 0.9062 | 0.4910 | 0.8986 |
| C16B | 1.0154 | 0.5341 | 0.8712 |
| C17B | 1.0446 | 0.5097 | 0.8050 |
| C18B | 1.1810 | 0.6399 | 0.8832 |
| C19B | 1.2840 | 0.7181 | 0.9153 |
| C20B | 1.3445 | 0.7419 | 0.9829 |
| C21B | 1.4508 | 0.8107 | 1.0105 |
| C22B | 1.4933 | 0.8583 | 0.9726 |
| O13C | 0.8728 | 0.7087 | 1.0120 |
| O14C | 1.0666 | 0.6951 | 1.0509 |
| C1C | 0.7690 | 0.5603 | 0.4498 |
| C2C | 0.9446 | 0.6828 | 0.5318 |
| C3C | 0.8120 | 0.6271 | 0.5246 |
| C4C | 0.5652 | 0.4460 | 0.3801 |
| C5C | 0.6246 | 0.5184 | 0.4470 |
| C6C | 0.8530 | 0.4979 | 0.4332 |
| C7C | 0.9685 | 0.7917 | 1.1316 |
| C8C | 0.8570 | 0.6898 | 1.1866 |

TABLE 5-continued

| Atom | X | Y | Z |
|---|---|---|---|
| C9C | 0.9736 | 0.7551 | 1.1883 |
| C10C | 1.1140 | 0.9052 | 1.0993 |
| C11C | 1.0928 | 0.8630 | 1.1502 |
| C12C | 0.9629 | 0.7271 | 1.0581 |
| H1C | 0.7373 | 0.6351 | 0.4107 |
| C17A | 0.5743 | 0.8576 | 0.6817 |
| C18A | 0.3450 | 0.8447 | 0.6976 |
| C19A | 0.2074 | 0.8178 | 0.7076 |
| C20A | 0.1562 | 0.7380 | 0.7022 |
| C21A | 0.0304 | 0.7147 | 0.7157 |
| C22A | −0.0485 | 0.7716 | 0.7351 |
| C23A | 0.0000 | 0.8505 | 0.7380 |
| C24A | 0.1266 | 0.8733 | 0.7242 |
| C25A | −0.1862 | 0.7457 | 0.7489 |
| C26A | −0.3437 | 0.7303 | 0.8269 |
| C27A | −0.1039 | 0.7825 | 0.8731 |
| H2A | 0.9429 | 0.9077 | 0.6056 |
| H5A | 1.0531 | 1.2020 | 0.5996 |
| H7A | 0.7037 | 1.1350 | 0.6649 |
| H11A | 1.3508 | 1.0045 | 0.5305 |
| H13A | 1.0143 | 1.3283 | 0.6699 |
| H13B | 0.9021 | 1.3656 | 0.6495 |
| H13C | 0.9558 | 1.2995 | 0.5907 |
| H14A | 1.6625 | 0.8097 | 0.4087 |
| H14B | 1.7455 | 0.7617 | 0.4375 |
| H14C | 1.7180 | 0.8448 | 0.4888 |
| H15A | 0.5496 | 1.0093 | 0.6392 |
| H15B | 0.6098 | 1.0457 | 0.7191 |
| H17A | 0.6609 | 0.8537 | 0.6757 |
| H20A | 0.2079 | 0.6995 | 0.6892 |
| H21A | −0.0027 | 0.6607 | 0.7119 |
| H23A | −0.0528 | 0.8885 | 0.7493 |
| H24A | 0.1586 | 0.9267 | 0.7260 |
| C23B | 1.4293 | 0.8360 | 0.9069 |
| C24B | 1.3255 | 0.7665 | 0.8778 |
| C25B | 1.6190 | 0.9253 | 0.9936 |
| C26B | 1.6008 | 0.9733 | 1.1221 |
| C27B | 1.8027 | 1.0251 | 1.0738 |
| H4B | 0.7471 | 0.4913 | 1.0036 |
| H6B | 0.7120 | 0.2888 | 0.7500 |
| H8B | 0.3909 | 0.2354 | 0.8380 |
| H11B | 0.3459 | 0.3823 | 1.0729 |
| H13D | 0.3750 | 0.1134 | 0.7475 |
| H13E | 0.3553 | 0.0961 | 0.6668 |
| H13F | 0.3107 | 0.1710 | 0.7209 |
| H14D | 0.1733 | 0.5046 | 1.3077 |
| H14E | 0.2115 | 0.5318 | 1.3890 |
| H14F | 0.2531 | 0.4548 | 1.3361 |
| H15C | 0.9411 | 0.4809 | 0.9385 |
| H15D | 0.8430 | 0.5248 | 0.9140 |
| H17B | 1.0003 | 0.4608 | 0.7686 |
| H20B | 1.3144 | 0.7121 | 1.0103 |
| H21B | 1.4937 | 0.8245 | 1.0554 |
| H23B | 1.4558 | 0.8681 | 0.8807 |
| H24B | 1.2837 | 0.7526 | 0.8326 |
| H26D | 1.5086 | 0.9682 | 1.1100 |
| H26E | 1.6371 | 1.0254 | 1.1600 |
| H26F | 1.6115 | 0.9291 | 1.1364 |
| H27D | 1.8461 | 1.0083 | 1.0325 |
| H27E | 1.8540 | 1.0224 | 1.1126 |
| H27F | 1.7939 | 1.0807 | 1.0850 |
| O1C | 0.7831 | 0.6012 | 0.4018 |
| O2C | 0.9404 | 0.7581 | 0.5441 |
| O3C | 1.0462 | 0.6593 | 0.5261 |
| O4C | 0.4498 | 0.4070 | 0.3877 |
| O5C | 0.6139 | 0.4260 | 0.3268 |
| O6C | 0.9247 | 0.4868 | 0.3879 |
| O7C | 0.8368 | 0.4575 | 0.4756 |
| O8C | 0.8560 | 0.8242 | 1.1341 |
| O9C | 0.8059 | 0.6897 | 1.2373 |
| O10C | 0.8179 | 0.6314 | 1.1240 |
| O11C | 1.0582 | 0.8819 | 1.0424 |
| O12C | 1.2146 | 0.9688 | 1.1232 |
| H2C | 1.0152 | 0.7857 | 0.5473 |
| H3C1 | 0.7469 | 0.6602 | 0.5362 |
| H3C2 | 0.8145 | 0.6003 | 0.5580 |
| H4C | 0.4185 | 0.3675 | 0.3509 |
| H5C1 | 0.6173 | 0.4999 | 0.4859 |
| H5C2 | 0.5726 | 0.5594 | 0.4542 |
| H7C | 0.8829 | 0.4237 | 0.4665 |
| H8C | 0.7896 | 0.7867 | 1.1250 |
| H9C1 | 1.0507 | 0.7320 | 1.1849 |
| H9C2 | 0.9867 | 0.8001 | 1.2339 |
| H10C | 0.7536 | 0.5974 | 1.1257 |
| H11C | 1.0887 | 0.9043 | 1.1959 |
| H11D | 1.1693 | 0.8413 | 1.1548 |
| H12C | 1.2238 | 0.9912 | 1.0946 |
| H14G | 1.0601 | 0.6609 | 1.0106 |

The DSC of the N-2 form of the citric acid co-crystal showed a variable endotherm at about 180°C, which represented a variable melt with decomposition. The TGA of the succinic acid co-crystal showed negligible weight loss up to 150° C.

The analytical data for each of the co-crystals described herein were obtained using the following procedures.

Single Crystal Data

For citric acid co-crystal formsdisclosed herein, a Bruker X8 APEX II CCD diffractometer equipped with a MICRO-STAR-H microfocus rotating anode X-ray generator of monochromatic Cu Kα radiation (2-1.54178 Å) was used to collect diffraction data at room temperature. For succinic acid cocrystal form, a Bruker X8 Prospector Ultra diffractometer equipped with IuS microfocus X-ray source of monochromatic Cu Kα radiation (2=1.54178 Å) and APEX II detector was used to collect diffraction data at room temperature. Indexing and processing of the measured intensity data were carried out with the APEX2 program suite (Bruker AXS, Inc., 5465 East Cheryl Parkway, Madison, WI 53711 USA). The final unit cell parameters were determined using the full data set. The structures were solved by direct methods and refined by full-matrix least-squares approach using the SHELXTL software package (G. M. Sheldrick, SHELXTL v6.14, Bruker AXS, Madison, WI USA.). Structure refinements involved minimization of the function defined by $\Sigma w(|F_o|-|F_c|)^2$, where w is an appropriate weighting factor based on errors in the observed intensities, $F_o$ is the structure factor based on measured reflections, and $F_c$ is the structure factor based on calculated reflections. Agreement between the refined crystal structure model and the experimental X-ray diffraction data is assessed by using the residual factors $R=>|F_o|-|F_c||/\Sigma|F_o|$ and $wR=[\Sigma w(|F_o|-|F_c|)^2/\Sigma w|F_o|]^{1/2}$. Difference Fourier maps were examined at all stages of refinement. All non-hydrogen atoms were refined with anisotropic thermal displacement parameters. Hydrogen atoms were generally calculated using idealized geometry, refined isotropically, and included in structure factor calculations with fixed parameters. There were a few exceptions where hydrogen atoms were located from the difference Fourier maps and refined isotropically, such as acidic hydrogen atoms of succinic acid in co-crystal structure.

PXRD

PXRD data were obtained using a Bruker C2 GADDS (General Area Detector Diffraction System). The radiation was Cu Kα (40 KV, 40 mA). The sample-detector distance was 15 cm. Samples were placed in sealed glass capillaries with diameters of ≤ 1 mm. The capillary was rotated during data collection. Transmission data were collected for approximately $2 \leq 2\theta < 32°$ with a sample exposure time of at least 1000 seconds. The resulting two-dimensional diffraction arcs were integrated to create a traditional 1-dimensional PXRD pattern with a step size of 0.05 degrees 2θ in the approximate range of 2 to 32 degrees 2θ.

DSC

TA INSTRUMENT® models Q2000, Q1000, or 2920 were used to generate DSC data. The measurement was made using standard TA Instruments hermetic pans. The measurement was made at a heating rate of 10° C./min, in a nitrogen environment from room temperature to 300° C., with a sample size of about 2-10 mg. The DSC plot was made with the endothermic peaks pointing down.

TGA

TA INSTRUMENT® models Q5000, Q500, or 2950 were used to generate TGA data. The measurement was made using standard TA Instruments Platinum pans. The measurement was made at a heating rate of 10° C./min, in a nitrogen environment from room temperature to 300° C., with a sample size about 10-30 mg.

Solid-State Nuclear Magnetic Resonance (SSNMR)

All solid-state C-13 NMR measurements were made with a Bruker DSX-400, 400 MHz NMR spectrometer. High resolution spectra were obtained using high-power proton decoupling and the TPPM pulse sequence and ramp amplitude cross-polarization (RAMP-CP) with magic-angle spinning (MAS) at approximately 12 kHz (A.E. Bennett et al, J. Chem. Phys., 1995, 103, 6951), (G. Metz, X. Wu and S.O. Smith, J. Magn. Reson. A,. 1994, 110, 219-227). Approximately 70 mg of sample, packed into a canister-design zirconia rotor, was used for each experiment. Chemical shifts (δ) were referenced to external adamantane with the high frequency resonance being set to 38.56 ppm (W.L. Earl and D.L. VanderHart, J. Magn. Reson., 1982, 48, 35-54).

Raman Spectroscopy

Raman spectra were acquired at a resolution of 4 $cm^{-1}$ with 64 scans co-added, using a IS50 FT-Raman spectrophotometer. The wavelength of the laser excitation was 1064 nm. A CaF2 beam splitter and a high sensitivity InGaS detector were used.

IR Spectroscopy

Infra-red spectra were acquired at a resolution of 4 $cm^{-1}$ with 64 scans co-added, using a IS50 FT-IR Spectrophotometer, incorporating a KBr beam-splitter and DTGS detector. Sample preparation was via the attenuated total reflectance method (ATR) using a single-bounce diamond ATR sampling accessory. An ATR correction step was included to correct the path length.

DISSOLUTION DATA:

The dissolution of the N-1 form of the citric acid and the succinic acid co-crystals of the compound of formula (I) were tested against that of the free form of the compound of formula (I). The dissolution properties, rate and extent, and peak solubility were tested in FaSSIF (fasted state simulated intestinal fluid).

This experiment was performed on a pION Microdissolution Profiler™ an API sparing, low volume dissolution instrument with UV fiber optics (UVFO) probes to measure real-time dissolution profile in biorelevant media. The experimental was run under the following conditions:

Apparatus: pIon Microdissolution profiler
Media: FaSSIF, pH 6.5
Volume: 15 mL at 37° C.
Stirring: 150 rpm with small stirrer bar
Dose: API powder at 0.2 mg/mL or 3 mg/vial
Study duration: 180 min
Time points: several time points to capture initial dissolution rate and through 180 min (typical time for absorption)

The results were analyzed using UVFO Analysis: Standard curve range 0-3 μg/mL; 10 mm path length probe windows; detection wavelength 315 nm; slope ~17 μg/mL/AU; R2=0.99.

Figure 15:
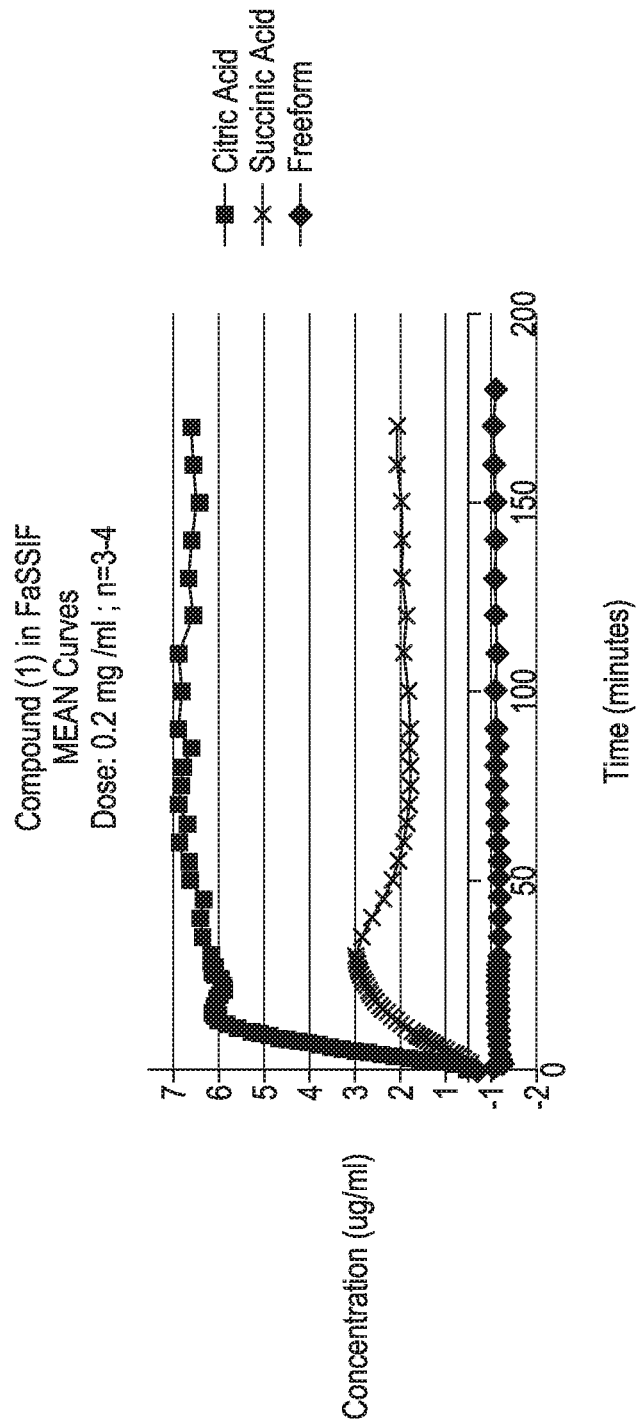
FIG. 15 shows the dissolution of the citric acid and the succinic acid co-crystals of the compound of formula (I) versus the dissolution of the free form of the compound of formula (I).

The results are shown in FIG. 15, and in Table 6 below.

The dissolution of both the succinic and the citric acid co-crystals in FaSSIF was better than the free form. The citric acid co-crystal has 3-4 times faster dissolution rate, AUC (extent of dissolution) and peak solubility compared to the succinic acid co-crystal.

In Vivo Performance:

To demonstrate the ability of the cocrystal to be absorbed a pharmacokinetic study was conducted in the dog model. The co-crystals were tested using the following formulations:

1. Succinic Acid co-crystal capsule (5 mg dose)—Pentagastrin pre-treated, fasted dogs
2. Citric Acid co-crystal capsule (5 mg dose)—Pentagastrin pre-treated, fasted dogs The Study Design is as follows:

Crossover in 4 fasted male dogs (~10 kg); dose 5 mg/dog; flush with 50 mL water; 2-week washout between treatments; 8 blood sample points per treatments.

Figure 16:
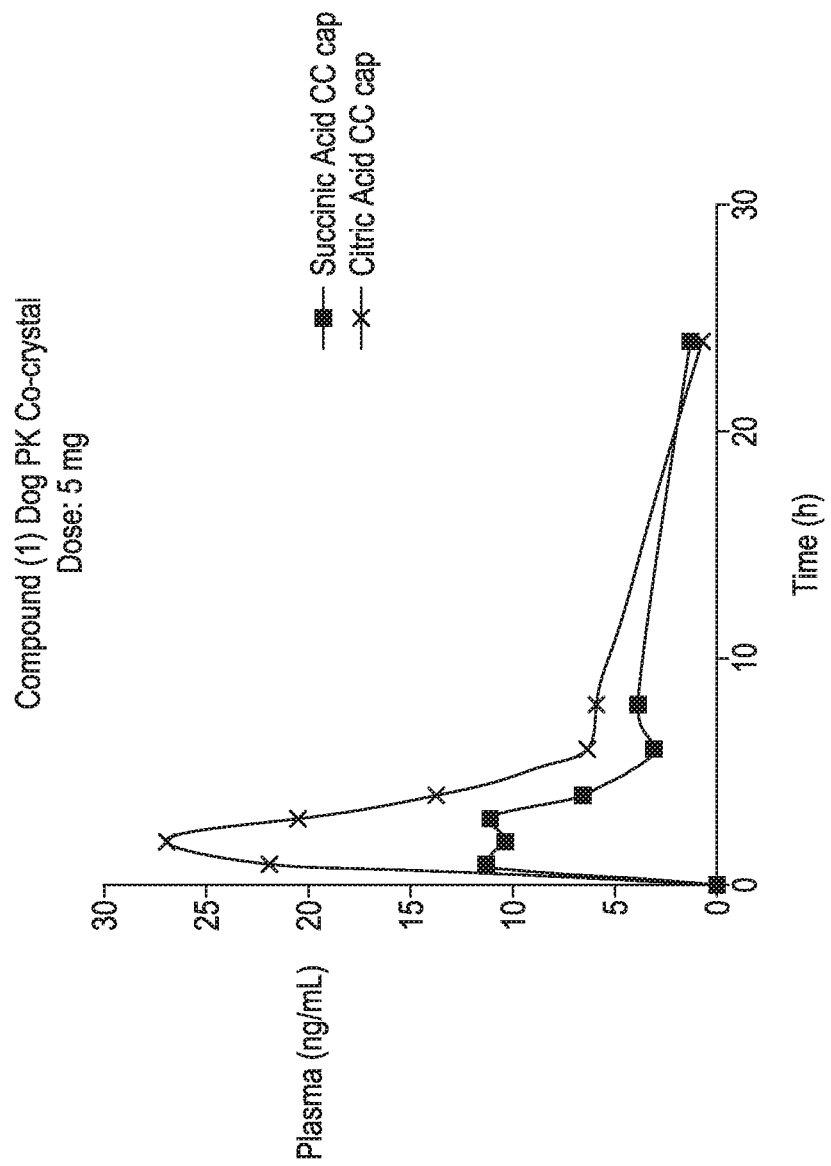
FIG. 16 show the pharmacokinetics (PK) profile of the citric acid and the succinic acid co-crystals of the compound of formula (I) in the dog.

The results are shown in Tables 7, and FIG. 16.

The citric acid co-crystal and the succinic acid co-crystal exhibit measurable systemic absorption in the dog model at relevant doses. The bioavailability ranged from 32-55% relative to a well absorbed reference formulation.

PK variability (% CV) of both co-crystal capsules was high, primarily due to one dog showing very low/undetectable blood levels.

Numerous modifications and variations of the present invention are possible in light of the above teachings. It is therefore to be understood that within the scope of the appended claims, the invention may be practiced otherwise than as specifically described herein.

TABLE 6 dissolution of co-crystals of the compound of Formula (I) and the free form

| | Mean Data N = 4 | | | | | |
|---|---|---|---|---|---|---|
| | AUC (μg · min/mL) | | | Dissolution Rate (μg/mL/min) | | Peak Solubility (μg/mL) |
| | Mean | SD | % CV | Mean | SD | Mean |
| Succinic Acid | 272.622 | 59.446 | 21.805 | 0.144 | 0.010 | 2.456 |
| Citric Acid | 988.900 | 153.850 | 15.558 | 0.584 | 0.093 | 6.358 |
| Free form | 0 | 0 | 0 | 0 | 0 | 0 |

\* All free form values were below limit of detection, i.e. no signal.
AUC - Area under the curve (calculated by trapezoidal rule),
SD - standard deviation
CV - coefficient of variation
Citric acid co-crystal N-1 form

TABLE 7

| | | PK Parameter Table | | | | | | |
|---|---|---|---|---|---|---|---|---|
| | Dose | Cmax (ng/mL) | | | AUC$_{0-24h}$ (ng·h/mL) | | BA (%) | |
| | (mg) | Mean | Std Dev | Tmax (h) | Mean | Std Dev | Mean | Std Dev | CV (%) |
| Succinic Acid Co-Crystal cap. | 5 | 12.22 | 9.52 | 1.5 | 93.97 | 66.64 | 31.94 | 22.65 | 70.92 |
| Citric Acid Co-crystal Cap | 5 | 29.28 | 20.51 | 2.0 | 161.61 | 107.98 | 54.93 | 36.70 | 66.82 |

Cmax - maximum plasma concentration in the time-couirse profile
AUC - area under the curve from time 0-24 h
BA - bioavailability relative to a well absorbed referencxe formulation
CV - coefficient of variation
Citric acid co-crystal N-1 form

What is claimed is:

1. A co-crystal of the compound of Formula (1)

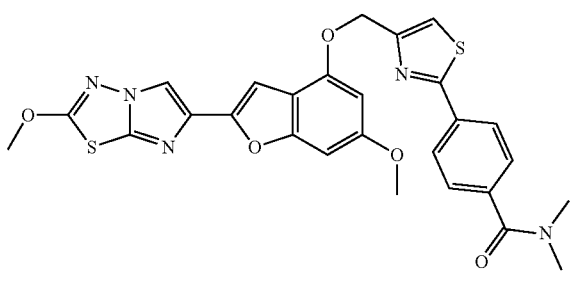

(I)

and a co-former, wherein the co-former is succinic acid or citric acid.

2. The co-crystal of claim 1, wherein the co-former is succinic acid.

3. The co-crystal of claim 2, wherein the co-crystal is characterized by one or more of the following:
   a) single crystal structure having unit cell parameters substantially equal to

| Crystal system, space group | Triclinic, P-1 | |
|---|---|---|
| Unit cell dimensions | a = 7.5 ± 0.5 Å | alpha = 103 ± 1° |
| | b = 9.6 ± 0.5 Å | beta = 92 ± 1° |
| | c = 20.1 ± 0.5 Å | gamma = 98 ± 1° |
| Volume | 1401 ± 30 Å$^3$ | |
| formula units per unit cell | 2 | | wherein measurement of the single crystal structure is at room temperature;
   b) an observed PXRD pattern substantially as shown in FIG. 1;
   c) a PXRD pattern comprising 4 or more 2θ values selected from 4.5±0.2, 9.5±0.2, 14.6±0.2, 16.3±0.2, 17.6±0.2, 21.4±0.2, 22.4±0.2, and 25.9±0.2, (obtained at room temperature and (CuKα λ=1.5418 Å);
   d) an infrared spectra substantially as shown in FIG. 5; and/or
   e) a FT-Raman spectra substantially as shown in FIG. 4 FIG. 6.

4. The co-crystal of claim 3, wherein ratio of the compound of formula (I) to succinic acid is 1:0.5.

5. The co-crystal of claim 1, wherein the co-former is citric acid.

6. The co-crystal of claim 5, wherein the co-crystal is in the N-1 form and is characterized by one or more of the following:
   a) single crystal structure having unit cell parameters substantially equal to

| Crystal system, space group | Triclinic, P-1 | |
|---|---|---|
| Unit cell dimensions | a = 10.3 ± 0.5 Å | alpha = 94 ± 1° |
| | b = 12.3 ± 0.5 Å | beta = 98 ± 1° |
| | c = 13.9 ± 0.5 Å | gamma = 98 ± 1° |
| Volume | 1717 ± 30 Å$^3$ | |
| formula units per unit cell | 2; | | b) a PXRD pattern substantially as shown in FIG. 6; and/or
   c) a PXRD pattern comprising four or more 2θ values (CuKα A=1.5418 Å at room temperature) selected from 6.4±0.2, 12.7±0.2, 14.4±0.2, 17.1±0.2, 23.9±0.2, 25.010.2, and 26.6±0.2.

7. The co-crystal of claim 6, wherein the ratio of the compound of formula (I) to citric acid is 1:1.

8. The co-crystal of claim 6, consisting essentially of Form N-1.

9. The co-crystal of claim 5, wherein the co-crystal is in the N-2 form and is characterized by one or more of the following:
   a) single crystal structure having unit cell parameters substantially equal to

| Crystal system, space group | Triclinic, P-1 | |
|---|---|---|
| Unit cell dimensions | a = 10.4 ± 0.5 Å | alpha = 111 ± 1° |
| | b = 17.8 ± 0.5 Å | beta = 93 ± 1° |
| | c = 20.5 ± 0.5 Å | gamma = 102 ± 1° |
| Volume | 3462 ± 30 Å$^3$ | |
| formula units per unit cell | 4 | | wherein measurement of the single crystal structure is at room temperature;
   b) a PXRD pattern substantially as shown in FIG. 12; and/or
   c) a PXRD pattern comprising four or more 2θ values (CuKα 2=1.5418 Å at room temperature) selected from 4.6±0.2, 5.5±0.2, 8.4±0.2, 11.3±0.2, 14.6±0.2, 16.4±0.2, 21.1±0.2, 24.2±0.2, and 25.2±0.2.

10. The co-crystal of claim 9, wherein the ratio of the compound of formula (I) to citric acid is 1:1.

11. The co-crystal of claim 9, consisting essentially of Form N-2.

12. The co-crystal of claim 1, in substantially pure form.

13. A pharmaceutical composition, which comprises a pharmaceutically acceptable carrier and a co-crystal as defined in claim 1, alone or in combination with another therapeutic agent.

14. A pharmaceutical composition, which comprises a pharmaceutically acceptable carrier and a co-crystal as defined in claim 3, alone or in combination with another therapeutic agent.

15. A pharmaceutical composition, which comprises a pharmaceutically acceptable carrier and a co-crystal as defined in claim 6, alone or in combination with another therapeutic agent.

16. A pharmaceutical composition, which comprises a pharmaceutically acceptable carrier and a co-crystal as defined in claim 9, alone or in combination with another therapeutic agent.

* * * * *